(12) United States Patent
Marcuccio et al.

(10) Patent No.: US 6,399,779 B1
(45) Date of Patent: Jun. 4, 2002

(54) ARYL BORATES

(75) Inventors: Sebastian Mario Marcuccio, Endeavour Hills; Mary Rodopoulos, Burwood East; Helmut Weigold, Mount Waverley, all of (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/215,319

(22) Filed: Dec. 18, 1998

Related U.S. Application Data

(63) Continuation-in-part of application No. PCT/AU98/00245, filed on Apr. 9, 1998.

(30) Foreign Application Priority Data

| Apr. 9, 1997 | (AU) | PO6096 |
| Jun. 20, 1997 | (AU) | PO7479 |
| Aug. 20, 1997 | (AU) | PO8675 |

(51) Int. Cl.$^7$ .......................................... C07D 213/22
(52) U.S. Cl. ................... 546/257; 549/456; 549/469; 562/45; 558/288
(58) Field of Search ................ 546/255, 257, 546/290; 549/430, 448, 456, 464, 469; 562/30, 35, 45, 7; 558/286, 288, 298

(56) References Cited

U.S. PATENT DOCUMENTS

| 5,550,236 A | * | 8/1996 | Schlosser et al. | 544/238 |
| 5,686,608 A | * | 11/1997 | Haber et al. | 544/316 |
| 5,919,930 A | * | 7/1999 | Haber et al. | 544/238 |

OTHER PUBLICATIONS

CA:113:132868 abs of Polym Prep 31(1) pp. 516–517 by Cramer, 1990.*
CA:125:166891 abs of J Org Chem by Guiles 61 (15) pp. 5169–5171, 1996.*
CA:115:208663 abs of Polym Prep by Perec et al 32 (1) pp. 329–330, 1991.*
CA:122L187077 abs of J Org Chem bu Percec et al 60(4) pp. 1060–1065, 1995.*
Giroux et al., Tetrahedron Letters, 38(22):3841–3844 (1997).
Ishiyama et al., Journal of Organic Chemistry, 60:7508–7510 (1995).
Pittre et al., Tetrahedron Letters, 38(7):1197–1200 (1997).
Ishiyana et al., Tetrahedron Letters, 38(19):3447–3450 (1997).
Todd et al., Tetrahedron Letters, 38(38):6781–6784 (1997).
Ishiyama et al., Journal of the American Chemical Society, 115:11018–11019 (1993).
Hu et al., Macromolecules 29:1082–1084 (1996).
Ramalingam et al., Organic Preparations and Procedures Int., 23(6):729–734 (1991).
Kobayashi et al., Journal of Organic Chemistry 61:5391–5399 (1996).
Miyaura et al., A. Chem. Rev., 95:2457–2483 (1995).

* cited by examiner

Primary Examiner—Jean F. Vollano
(74) Attorney, Agent, or Firm—Bacon & Thomas

(57) ABSTRACT

The invention provides a process for covalently coupling organic compounds which comprises reacting an aromatic ring compound having a halogen substituent or other substituent which undergoes substitution with a diboronic acid ester at a coupling position with a diboron derivative in the presence of a Group VIII metal catalyst and a suitable base.

45 Claims, No Drawings

ARYL BORATES

This application is a continuation-in-part application of pending international application number PCT/AU97/00245 filed Apr. 9, 1998.

This invention relates to a process for covalently coupling organic compounds, in particular to a process for covalently linking aromatic ring compounds via an organoboron intermediate to other organic compounds. The invention also relates to a process for the preparation of the organoboron intermediates.

Processes for forming covalent bonds between aromatic ring compounds and organic compounds, both inter- and intra-molecular, are of particular importance to the synthetic organic chemist. Many such reactions are known, each requiring its own special reaction conditions, solvents, catalysts, ring activating groups etc. Some known types of coupling reactions which can involve aromatic ring compounds include the Grignard reaction, Heck reactions and Suzuki reactions (N. Miyaura and A. Suzuki, Chem. Rev. 1995, 95, 2457–2483).

Catalysts of palladium, its complexes and its salts are well recognised for activation of C—H bonds towards coupling reactions. In this regard the Heck reaction of an aryl halide with an aryl or vinyl halide in the presence of palladium derivatives has been the subject of intensive study. However commercial development of the Heck reaction has not progressed as rapidly as could have been expected. Other Group VIII metal catalysts, such as platinum, have also been used to activate such carbon bonds.

Substituted bi- and tri-aryl compounds are of great interest to the pharmaceutical and agrochemical industries. A great number of these compounds have been found to possess pharmaceutical activity, while others have been found to be useful herbicides. There is also interest from the polymer industry in polymers prepared by the linking together of aromatic ring compounds.

Conventional methods for covalently linking aromatic rings, such as by reaction of an appropriate Grignard reagent, involve harsh conditions and are not suitable for aromatic rings with active hydrogen containing substituents. Substituents with active hydrogen atoms also can become involved in unwanted side reactions leading to undesirable products. Such substituents need to be protected prior to reaction. Boronic acid derivatives required for the Suzuki reaction are traditionally synthesized through highly reactive organo metallic intermediates.

In view of the severity of the reaction conditions the range of substituents which could be present during the linking reaction was considerably limited, and the range of useful reaction media (solvents) was restricted to those which are generally expensive, difficult to remove and/or toxic.

Other difficulties associated with the known coupling reactions are the high temperatures required and the lack of control of the functionality of the products, leading to complex mixtures which can be difficult to separate.

It has now been found that coupling of aromatic ring compounds to other organic compounds can be achieved via an arylboron intermediate in the presence of a Group VIII metal catalyst and a suitable base.

Accordingly the invention provides a process for covalently coupling organic compounds which comprises reacting an aromatic ring compound having a halogen or halogen-like substituent at a ring coupling position with a diboron derivative in the presence of a Group VIII metal catalyst and a suitable base.

In one embodiment this process may be used to prepare a symmetrical product by reacting the diboron derivative with about two equivalents of aromatic ring compound. In this embodiment the coupling proceeds in two steps. In the first step the diboron derivative reacts with about one equivalent of aromatic ring compound in the presence of the Group VIII metal catalyst and suitable base to form an arylboron intermediate, which intermediate reacts in the presence of base with the remaining equivalent of aromatic ring compound. According to this embodiment the covalent coupling comprises a covalent bond between ring coupling positions of two molecules of aromatic ring compound.

Preferably the suitable base used to catalyse the reaction with the boron derivative is also able to catalyse the coupling of the arylboron intermediate to the remaining aromatic compound. However, if necessary, a stronger base can be added after the formation of the arylboron intermediate to catalyse the coupling reaction.

The process according to the invention also allows the preparation of unsymmetrical products. Accordingly in another embodiment of the invention there is provided a process for covalently coupling organic compounds which comprises:

reacting an aromatic ring compound having a halogen or halogen-like substituent at a ring coupling position with a diboron derivative in the presence of a Group VIII catalyst and a suitable base to form an arylboron intermediate, and reacting the arylboron intermediate with an organic compound having a halogen or halogen-like substituent at a coupling position in the presence of a Group VIII metal catalyst and a suitable base, whereby the aromatic ring compound is coupled to the organic compound via a direct bond between the respective coupling positions.

The process according to this embodiment allows the preparation of unsymmetrical compounds when the organic compound is different from the aromatic ring compound, although symmetrical products will be obtained if the organic compound is the same as the aromatic ring compound.

It is especially convenient to conduct the process in a single pot without isolation of the arylboron intermediate, however it has been found that the presence of unreacted diboron derivative can interfere with the coupling step, resulting in the formation of unwanted by-products.

Accordingly in another embodiment of the present invention there is provided a process for covalently coupling organic compounds which comprises:

reacting an aromatic ring compound having a halogen or halogen-like substituent at a ring coupling position with a diboron derivative in the presence of a Group VIII metal catalyst and a suitable base to form an arylboron intermediate, adding water and a suitable base to decompose excess diboron derivative, reacting the arylboron intermediate with an organic compound having a halogen or halogen-like substituent at a coupling position in the presence of a Group VIII metal catalyst and a suitable base, whereby the aromatic ring compound is coupled to the organic compound via a direct bond between respective coupling positions.

Preferably the reaction is conducted in a single pot, although it is possible to isolate the arylboron intermediate prior to the final coupling step. If the reaction is conducted in a single pot it is preferred that the base added to decompose the diboron derivative is suitable for catalysing the coupling reaction. In this case there is no need to add further base with the organic compound in the coupling reaction.

In cases where there is a need to remove excess diboron derivative but the use of water and/or base is deleterious because of the sensitivity of substituents, etc, or other factors the excess diboron derivative may be decomposed by addition of mild oxidising agents following the formation of the arylboron intermediate.

Accordingly in a further embodiment there is provided a process for covalently coupling organic compounds which comprises:

reacting an aromatic ring compound having a halogen or halogen-like substituent at a ring coupling position with a diboron derivative in the presence of a Group VIII metal catalyst and a suitable base to form an arylboron intermediate;

adding a mild oxidising agent to decompose excess diboron derivative;

reacting the arylboron intermediate with an organic compound having a halogen or halogen-like substituent at a coupling position in the presence of a Group VIII metal catalyst and a suitable base whereby the aromatic ring compound is coupled to the organic compound via a direct bond between respective coupling positions.

The mild oxidising agent may be any compound which will break the B—B bond of the diboron derivative but which is not strong enough to break boron-carbon bonds of the arylboron intermediate. Suitable mild oxidising agents are N-chlorosuccinimide, dimethyl dioxirane, dioxygen gas, chloramine-T, chloramine-B, 1-chlorotriazole, 1,3-dichloro-5,5-dimethylhydantoin, trichloroisocyanuric acid and dichloroisocyanuric acid potassium salt.

Oxidants such as hydrogen peroxide, ozone, bromine, t-butyl hydroperoxide, potassium persulphate, sodium hypochlorite and peracids, are too strong for use in this process; use of strong oxidants does not form part of this invention.

The term "aromatic ring compound(s)" as used herein refers to any compound which includes or consists of one or more aromatic or pseudoaromatic rings. The rings may be carbocyclic or heterocyclic, and may be mono or polycyclic ring systems. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuran, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The term "aromatic ring compound(s)" includes molecules, and macromolecules, such as polymers, copolymers and dendrimers which include or consist of one or more aromatic or pseudoaromatic rings. The term "pseudoaromatic" refers to a ring system which is not strictly aromatic, but which is stablized by means of delocalization of π electrons and behaves in a similar manner to aromatic rings. Examples of pseudoaromatic rings include but are not limited to furan, thiophene, pyrrole and the like.

As used herein the term "organic compound having a halogen or halogen-like substituent at a coupling position" refers to any organic compound having a carbon to halogen or carbon to halogen-like substituent bond at a position where coupling to the aromatic ring compound is desired. The organic compound may be aliphatic, olefinic, aromatic, polymeric or dendritic. The compound may be an aromatic ring compound as defined above or part of such an aromatic ring compound. The organic compound may have one or more, preferably between 1 and 6, halogen or halogen-like substituents at coupling positions.

The terms "olefinic" and "olefinic compound" as used herein refer to any organic compound having at least one carbon to carbon double bond which is not part of an aromatic or pseudo aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,diene, cyclohexa-1,3-diene, cyclohexa-1,4-diene, cyclohepta-1,3,5-triene and cycloocta-1,3,5,7-tetraene, each of which may be optionally substituted. Preferably the straight chain branched or cyclic alkene contains between 2 and 20 carbon atoms.

In one embodiment the organic compound is an olefinic compound of formula I

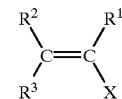

where R, $R^2$ and $R^3$ are each independently selected from alkyl, alkenyl, alkynyl, aryl, heteroaryl, acyl, arylalkyl and heteroarylalkyl, each of which may be optionally substituted: and cyano, isocyano, formyl, carboxyl, nitro, halo, alkoxy, alkenoxy, aryloxy, benzyloxy, haloalkoxy, haloalkenyloxy, haloaryloxy, nitroalkyl, nitroalkenyl, nitroalkynyl, arylamino, diarylamino, dibenzylamino, alkenylacyl, alkynylacyl, arylacyl, acylamino, diacylamino, acyloxy, alkylsulphonyloxy, arylsulphenyloxy, heterocycloxy, arylsulphenyl, carboalkoxy, carboaryloxy, alkylthio, benzylthio, acylthio, sulphonamide, sulfanyl, sulfo, carboxy (including carboxylato), carbamoyl, carboximidyl, sulfinyl, sulfinimidyl, sulfinohydroximyl, sulfonimidyl, sulfondiimidyl, sulfonohydroximyl, sulfamyl, phosphorous containing groups (including phosphinyl, phosphinimidyl, phosphonyl, dihydroxyphosphanyl, hydroxyphosphanyl, phosphone (including phosphonato) and hydrohydroxyphosphoryl), guanidinyl, duanidino, ureido and ureylene, and X is a halogen or halogen-like substituent.

The term "coupling position" as used herein refers to a position on an aromatic ring compound at which coupling to an organic compound is desired. A coupling position on a ring of an aromatic ring compound is also referred to as a "ring coupling position". The term "coupling position" also refers to a position on an organic compound at which coupling to an aromatic ring compound is desired. Each aromatic ring compound or organic compound may have one or more, preferably between 1 and 6, coupling positions.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxy silyl and arylphenoxy silyl.

The aromatic ring compound must include at least one halogen or halogen-like substituent at a ring coupling position to enable reaction with the diboron derivative. Similarly the organic compound must have at least one halogen or halogen-like substituent at a coupling position to enable reaction with the arylboron intermediate. Preferred halogen substituents include I and Br. Cl may also be used although Cl is generally less reactive to substitution by the boron derivative or aryl boron intermediate. The reactivity of chloro substituted aromatic ring compounds can be increased by selection of appropriate ligands on the Group VIII metal catalyst. The terms "halogen-like substituent" and "pseudo-halide" refer to any substituent which, if present on an aromatic ring, may undergo substitution with a diboron derivative in the presence of a Group VIII metal catalyst and base to give an arylboron intermediate, or if present on an organic compound may undergo substitution with an arylboron intermediate to give a coupled product. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0-471-95483-7).

The process according to the invention is especially suitable for coupling aromatic ring compounds which have active hydrogen containing substituents on the aromatic ring(s) to be coupled. The term "active hydrogen containing substituent" as used herein refers to a substituent which contains a reactive hydrogen atom. Examples of such substituents include but are not limited to hydroxy, amino, imino, acetyleno, carboxy (including carboxylato), carbamoyl, carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene. Of these substituents it is particularly surprising that the reaction can be conducted with hydroxy and amino substituents in view of their high reactivity. Carboxyl, sulfo and the like (i.e. acidic) substituents may require additional base.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-,2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including alkyl and cycloalkyl groups as previously defined which contain a triple bond, preferably $C_{2-20}$ alkynyl. Examples of alkynyl include ethynyl, 2,3-propynyl and 2,3- or 3,4-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylearbonyl and cyclohexylcarbonyt; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethaeryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocycic, heterocyclyl" and "heterocycl" as used herein on their own or as part of a group such as "heterocyclicalkenoyl", heterocycloxy" or "haloheterocyclyl" refer to aromatic, pseudo-aromatic and non-aromatic rings or ring systems which contain one or more heteroatoms selected from N, S, O and P and which may be optionally substituted. Preferably the rings or ring systems have 3 to 20 carbon atoms. The rings or ring systems may be selected from those described above in relation to the definition of "aromatic ring compound(s)".

The term "aryl" as used herein on its own or as part of a group such as "haloaryl" and "aryloxycarbonyl" refers to aromatic and pseudo-aromatic rings or ring systems composed of carbon atoms, optionally together with one or more heteroatoms. Preferably the rings or ring systems have between 3 and 20 carbon atoms. The rings or ring systems may be optionally substituted and may be selected from those described above in relation to the definition of "aromatic ring compound(s)".

The diboron derivative may be an ester or other stable derivative of diboronic acid. Examples of suitable esters include those of the formula $(RO)_2B—B(RO)_2$ where R is optionally substituted alkyl or optionally substituted aryl or $—B(OR)_2$ represents a cyclic group of formula

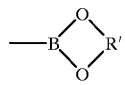

where R' is optionally substituted alkylene, arylene or other divalent group comprising linked aliphatic or aromatic moieties. Preferred diboron derivatives include the pinacol ester of diboronic acid, bis(ethanediolato)diboron, bis(n-propanediolato)diboron and bis(neopentanediolato)diboron. Some of the diboron derivatives will be more readily amenable to subsequent hydrolysis than others and may allow for the use of milder reaction conditions. Furthermore, judicious choice of the diboron derivative used may facilitate control over the reaction products formed. The diboron ester derivatives may be made following the method of Brotherton et al. [R. J. Brotherton, A. L. McCloskey, L. L. Peterson and H. Steinberg, *J. Amer. Chem. Soc.* 82, 6242 (196); R. J. Brotherton, A. L. McCloskey, J. L. Boone and H. M. Manasevit, *J. Amer. Chem. Soc.* 82, 6245 (1960)]. In this process $B(NMe_2)_3$, obtained by reaction of $BCl_3$ with $NHMe_2$, is converted to $BrB(NMe_2)_2$ by reaction with a stoichiometric amount of $BBr_3$. Reduction in refluxing toluene with sodium metal gives the diboron compound $[B(NMe_2)_2]_2$ which, after purification by distillation, can be reacted with the alcohol (for example, pinacol) in the presence of a stoichiometric amount of HCl to give the desired ester product. Bis(neopentanediolato)diboron is described by Nguyen et al [Nguyen, P., Lesley, G., Taylor, N. J., Marder, T. B., Pickett, N/L/, Clegg, W., Elsegood, M. R. J., and Norman, N. C., *Inorganic Chem.* 1994, 33, 4623–24]. Other methods for the preparation of the diboron derivatives would be known to those in the art. The diboron derivatives in Examples 1, 2 and 3 are known, but their use in the formation of aryl boron intermediates has not been disclosed.

The term "Group VIII metal catalyst" as used herein refers to a catalyst comprising a metal of Group VIII of the periodic table described in Chemical and Engineering News, 63(5), 27, 1985. Examples of such metals include Ni, Pt and Pd. Preferably the catalyst is a palladium catalyst as described below, although analogous catalysts of other Group VIII metals may also be used. Examples of suitable Ni catalysts include nickel black, Raney nickel, nickel on carbon and nickel clusters.

The palladium catalyst may be a palladium complex. Examples of suitable palladium catalysts include but are not limited to $PdCl_2$, $Pd(OAc)_2$, $PdCl_2(dppf)CH_2Cl_2$, $Pd(PPh_3)_4$, $Pd(Ph_2P(CH_2)_nPPh_2)$ where n is 2 to 4 and related catalysts which are complexes phosphine ligands, (such as $P(o\text{-tolyl})_3$, $P(i\text{-Pr})_3$, $P(cyclohexyl)_3$, $P(o\text{-MeOPh})_3$, $P(p\text{-MeOPh})_3$, dppp, dppb, TDMPP, TTMPP, TMPP, TMSPP and related water soluble phosphines), related ligands (such as triarylarsine, triarylantimony, triarylbismuth), phosphite ligands (such as $P(OEt)_3$, $P(O\text{-p-tolyl})_3$, $P(O\text{-o-tolyl})_3$ and $P(O\text{-iPr})_3$) and other suitable ligands including those containing P and/or N atoms for coordinating to the palladium atoms, (such as for example pyridine, alkyl and aryl substituted pyridines, 2,2'-bipyridyl, alkyl substituted 2,2'-bipyridyl and bulky secondary or tertiary amines), and other simple palladium salts either in the presence or absence of ligands. The palladium catalysts include palladium and palladium complexes supported or tethered on solid supports, such as palladium on carbon, as well as palladium black, palladium clusters, palladium clusters containing other metals, and palladium in porous glass described in J. Li, A. W-H. Mau and C. R. Strauss, Chemical Communications, 1997, p1275. The same or different palladium catalysts may be used to catalyse different steps in the process. In certain reactions there are advantages in using ligands with altered basicity and/or steric bulk.

The process may be performed in any suitable solvent or solvent mixture. Examples of such solvents include amides of the lower aliphatic carboxylic acids and lower aliphatic secondary amines, DMSO, aromatic hydrocarbons, nitromethane, acetonitrile, benzonitrile, ethers, polyethers, cyclic ethers, lower aromatic ethers, lower alcohols, and their esters with the lower aliphatic carboxylic acids, pyridine, alkylpyridines, cyclic and the lower secondary and tertiary amines, and mixtures thereof, including mixtures with other solvents.

In a preferred embodiment of the invention the process is performed in a protic solvent. Examples of suitable protic solvents include water and lower alcohols. Most preferably the solvent is water, ethanol, methanol, isopropanol or mixtures thereof with other solvents. Particularly preferred solvents are ethanol and methanol. Strict exclusion of water from the solvents is generally not essential. The addition of further diboron derivative has been found useful when the solvents are not anhydrous.

The temperature at which each step of the process according to the invention is conducted will depend on a number of factors including the desired rate of reaction, solubility and reactivity of the reactants in the selected solvent, boiling point of the solvent, etc. The temperature of the reaction will generally be in the range of −100 to 250° C. In a preferred embodiment the process is performed at a temperature between 0 and 120° C., more preferably between 0 and 80° C., and most preferably between 15 and 40° C.

The term "suitable base" as used herein refers to a basic compound which, when present in the reaction mixture, is capable of catalysing, promoting or assisting reaction between reactants. The base may be suitable for catalysing a single step, or more than one step, depending on the desired outcome of the reaction. For example a base may be chosen which catalyses reaction between the aromatic ring compound and the diboron derivative, but which is not strong enough to catalyse further reaction of aryl boron intermediate with additional aromatic ring compound or other organic compound. In this case a stronger base (and water) may be added to decompose excess diboron derivative, and which may also catalyse reaction of the arylboron intermediate with the organic compound. It is also preferable that a base is chosen which is soluble in the solvent to which it is added. Examples of bases which are suitable for catalysing the reaction of the aromatic ring compound with the diboron derivative include, aryl and alkyl carboxylates (for example potassium acetate), fluorides, hydroxides and carbonates of Li, Na, K, Rb, Cs, ammonium, alkylammonium, Mg, Ca, & Ba; phosphates and arylphosphates of Li, Na, K, Rb and Cs; phosphate esters (eg. $C_6H_5OP(O)(ONa)_2$) of Li, Na, K, Rb and Cs; phenoxides of Li, Na, K, Rb and Cs; alkoxides of Li, Na, K, Rb and Cs; and thallium hydroxide. Some of these bases may be used in conjunction with a phase transfer reagent, such as for example tetraalkylammonium salts or the crown ethers.

Examples of bases suitable for catalysing reaction of the aromatic ring compounds with the diboron derivative, without generally catalysing the further reaction of the arylboron intermediate, include aryl and alkyl carboxylates and phosphates of Li, Na, K, Rb, Cs, ammonium and alkylammonium.

Examples of bases suitable for decomposing excess diboron derivative and/or catalysing reaction of the arylboron intermediate include the stronger bases listed above, including caesium carbonate, potassium carbonate and alkali metal hydroxides.

The literature (cf. Miyaura et al., J. Org. Chem., 1995) describes the synthesis of arylboronic acid esters of pinacol using weak bases (viz. potassium acetate) at 80° C. With strong bases, (e.g. potassium carbonate) dimer formation occurred, the Suzuki reaction competing strongly with arylboronic acid ester formation.

It has now surprisingly been found that strong bases can be used to synthesise organoboron intermediates, such as arylboronic acid esters near or below ambient temperatures in good yields with good selectivity compared to biaryl formation. The temperature of the reaction using the strong base can be selected such that further reaction of the intermediates with unreacted aromatic ring compound having halogen or halogen-like substituents is substantially prevented. This has the advantage that it enables the preparation of the arylboronic acid ester at low temperatures, important when the substituent(s) on the aryl ring can react (be reduced, rearranged, etc). A further advantage of these reactions employing stronger base to form the arylboronic acid ester is that the arylboronic acid ester may be coupled with aryl halides to give symmetric or asymmetric biaryls or with alkenyl halides to give styrryl type species without the requirement of adding a second (strong) base. The promotion of these Suzuki coupling reactions is therefore controlled primarily by reaction temperature, the temperature required depending upon the reactivity towards coupling of the added halide species and the sensitivity/stability of substituents on the reactants. For example, after formation of the arylboron intermediate, the temperature of the reaction medium can be raised to promote the coupling reaction. The temperature of the reaction with the diboron derivative is preferably conducted at a temperature below 40° C., more preferably at or below ambient temperature.

As used herein the term "arylboron intermediate" refers to the product of the Group VIII metal base catalysed reaction between an aromatic ring compound having a halogen or halogen-like substituent at a ring coupling position and a diboron derivative, the product including a carbon- to -boron bond at the ring coupling position. Examples of such intermediates include arylboronic acid esters.

In another aspect of the invention there is provided a process for preparing an arylboron intermediate comprising reacting a diboron derivative with an aromatic ring compound having a halogen or halogen-like substituent and an active hydrogen containing substituent in the presence of a Group VIII metal catalyst and a suitable base.

In a further aspect of the invention there is provided a process for preparing an arylboron intermediate, comprising reacting a diboron derivative with an aromatic ring compound having a halogen or halogen-like substituent in a protic solvent in the presence of a Group VIII metal catalyst and a suitable base.

A first step in the purification of the arylboron intermediate so formed may be the decomposition of any excess diboron derivative by the use of water, water and base, or by the use of a mild oxidising agent.

In a further aspect of the invention there is provided a process for the preparation of an aryl boronic acid including hydrogenolysing or hydrolysing the arylboron intermediate as hereinbefore described using established procedures. The ease of hydrolysis/hydrogenolysis is a function of the diboronic ester used. Some aryl boron intermediates are more amenable to hydrolysis/hydrogenolysis than those derived from the pinacol ester of diboronic acid. This method only relates to arylboron intermediates which are boronic esters.

Some of the arylboron intermediates and aryl boronic acids are novel and represent a further aspect of the present invention. Examples of such novel aryl boron intermediates which may be prepared according to the present invention are listed in Table 2, while some known arylboron intermediates prepared in accordance with the present invention are listed in Table 1.

TABLE 1

KNOWN BORONATES PREPARED BY DIBORON METHODOLOGY

| Compound Number | COMPOUND STRUCTURE | Calc M/Z | Found M/z |
|---|---|---|---|
| 1 | H₃CO₂C–C₆H₄–Bpin | 262.1 | 262 (M$^+$)<br>247 (M$^+$ − 15) |
| 2 | H₃COC–C₆H₄–Bpin | 246.1 | 246 (M$^+$)<br>231 (M$^+$ − 15) |
| 3 | Cl–C₆H₄–Bpin | 238 | 238 (M$^+$)<br>223 (M$^+$ − 15) |
| 4 | pinB–C₆H₄–Bpin | 330.1 | 330 (M$^+$)<br>315 (M$^+$ − 15) |
| 5 | O₂N–C₆H₄–Bpin | 249.1 | 249 (M$^+$)<br>234 (M$^+$ − 15) |
| 6 | Ph–C₆H₄–Bpin | 280.2 | 280 (M$^+$)<br>265 (M$^+$ − 15) |
| 7 | 2-thienyl–Bpin | 210.1 | 210 (M$^+$)<br>195 (M$^+$ − 15) |
| 8 | 3,4-methylenedioxyphenyl–Bpin | 248.1 | 248 (M$^+$)<br>233 (M$^+$ − 15) |
| 9 | OHC–C₆H₄–Bpin | 232 | 233 (M$^+$ + 1) |
| 10 | Br–C₆H₄–Bpin | 282 | 282 (M$^+$ + 1) |
| 11 | NC–C₆H₄–Bpin | 229 | 230 (M$^+$ + 1) |

TABLE 1-continued

KNOWN BORONATES PREPARED BY DIBORON METHODOLOGY

| Compound Number | COMPOUND STRUCTURE | Calc M/Z | Found M/z |
|---|---|---|---|
| 12 | 2-nitrophenyl pinacol boronate | 249 | 250 (M$^+$ + 1) |
| 13 | 4-nitrophenyl pinacol boronate | 249 | 250 (M$^+$ + 1) |
| 14 | 4-chlorophenyl 1,3,2-dioxaborolane | 182 | 183 (M$^+$ + 1) |
| 15 | phenyl 5,5-dimethyl-1,3,2-dioxaborinane | 190 | 191 (M$^+$ + 1) |
| 16 | phenyl 1,3,2-dioxaborolane | 148 | 149 (M$^+$ + 1) |
| 17 | 4-(H$_2$NOC)phenyl pinacol boronate | 247.1 | 247 (M$^+$)<br>232 (M$^+$ − 15) |
| 18 | 3,5-bis(trifluoromethyl)phenyl pinacol boronate | 340.1 | 340 (M$^+$)<br>325 (M$^+$ − 15) |
| 19 | 4-(HO$_2$C)phenyl pinacol boronate | 248 | 249 (M$^+$ + 1) |
| 20 | 2-cyanophenyl 1,3,2-dioxaborinane | 187 | 188 (M$^+$ + 1) |
| 21 | 4-cyanophenyl 1,3,2-dioxaborinane | 187 | 188 (M$^+$ + 1) |
| 22 | 3-nitrophenyl pinacol boronate | 249 | 250 (M$^+$ + 1) |

TABLE 1-continued

KNOWN BORONATES PREPARED BY DIBORON METHODOLOGY

| Compound Number | COMPOUND STRUCTURE | Calc M/Z | Found M/z |
|---|---|---|---|
| 23 | F$_3$C-C$_6$H$_4$-B(OCH$_2$CH$_2$O) | 216 | 217 (M$^+$ + 1) |

TABLE 2

NOVEL BORONATES PREPARED BY DIBORON METHODOLOGY

| Compound Number | COMPOUND STRUCTURE | Calc M/Z | Found M/z |
|---|---|---|---|
| 24 | H$_3$CHNOC—C$_6$H$_4$—Bpin | 261.1 | 261 (M$^+$)<br>246 (M$^+$ − 15) |
| 25 | F—C$_6$H$_4$—Bpin | 222.1 | 222 (M$^+$)<br>207 (M$^+$ − 15) |
| 26 | H$_3$CO-pyridine(OCH$_3$)-Bpin | 265.1 | 265 (M$^+$) |
| 27 | pin B—C$_6$H$_4$—C$_6$H$_4$—Bpin | 406.1 | 406 (M$^+$)<br>391 (M$^+$ − 15) |
| 28 | H$_3$COCHN—C$_6$H$_4$—Bpin | 261.1 | 261 (M$^+$) |
| 29 | H$_3$CO$_2$C—C$_6$H$_3$(OCH$_3$)—Bpin | 292.1 | 292 (M$^+$)<br>277 (M$^+$ − 15) |
| 30 | Br—pyridine—Bpin | 283.0 | 285, 283 (M$^+$)<br>270, 268 (M$^+$ − 15) |
| 31 | H$_3$CO—C$_6$H$_3$(CH$_3$)—Bpin | 248.1 | 248 (M$^+$)<br>233 (M$^+$ − 15) |

TABLE 2-continued

NOVEL BORONATES PREPARED BY DIBORON METHODOLOGY

| Compound Number | COMPOUND STRUCTURE | Calc M/Z | Found M/z |
|---|---|---|---|
| 32 | 2,4-dimethylphenyl pinacol boronate | 232.1 | 232 (M$^+$) 217 (M$^+$ − 15) |
| 33 | 4-trifluoromethylphenyl pinacol boronate | 272.1 | 272 (M$^+$) 257 (M$^+$ − 15) |
| 34 | 4-tert-butylphenyl pinacol boronate | 260.1 | 260 (M$^+$) 245 (M$^+$ − 15) |
| 35 | 3,4,5-trimethoxyphenyl pinacol boronate | 294.2 | 294 (M$^+$) 279 (M$^+$ − 15) |
| 36 | 4-methoxy-2-methylphenyl pinacol boronate | 248.1 | 248 (M$^+$) 233 (M$^+$ − 15) |
| 37 | 2,4-dimethoxyphenyl pinacol boronate | 264.1 | 264 (M$^+$) 249 (M$^+$ − 15) |
| 38 | 3-thienyl pinacol boronate | 210.1 | 210 (M$^+$) 195 (M$^+$ − 15) |
| 39 | 4-sulfamoylphenyl pinacol boronate | 283 | 284 (M$^+$ + 1) |
| 40 | 4-amino-3-carboxyphenyl pinacol boronate | 263 | 264 (M$^+$ + 1) |

TABLE 2-continued

NOVEL BORONATES PREPARED BY DIBORON METHODOLOGY

| Compound Number | COMPOUND STRUCTURE | Calc M/Z | Found M/z |
|---|---|---|---|
| 41 | 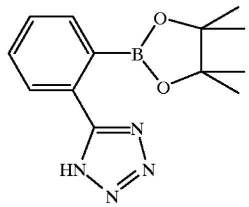 | 272 | 273 (M$^+$ +1) |
| 42 | 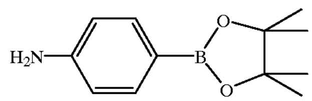 | 219 | 220 (M$^+$ + 1) |
| 43 | 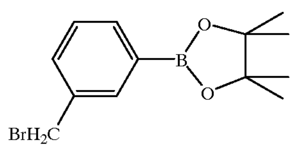 | 296 | 298 (M$^+$ + 2) |
| 44 | 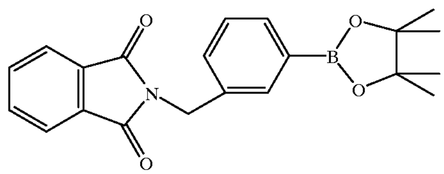 | 363 | 364 (M$^+$ + 1) |
| 45 | 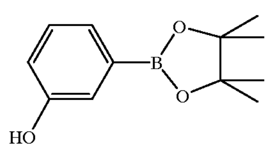 | 220 | 221 (M$^+$ + 1) |
| 46 | 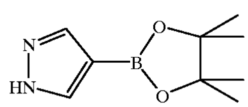 | 194 | 195 (M$^+$ + 1) |
| 47 | 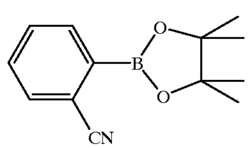 | 229 | 230 (M$^+$ + 1) |
| 48 | 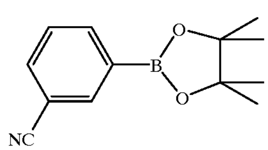 | 229 | 230 (M$^+$ + 1) |
| 49 | 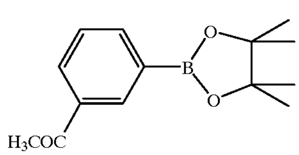 | 246 | 247 (M$^+$ + 1) |

TABLE 2-continued

NOVEL BORONATES PREPARED BY DIBORON METHODOLOGY

| Compound Number | COMPOUND STRUCTURE | Calc M/Z | Found M/z |
|---|---|---|---|
| 50 | 2-CN-C6H4-B(OCH2C(CH3)2CH2O) | 215 | 216 (M+ + 1) |
| 51 | 3-CN-C6H4-B(OCH2C(CH3)2CH2O) | 215 | 216 (M+ + 1) |
| 52 | 4-NC-C6H4-B(OCH2C(CH3)2CH2O) | 215 | 216 (M+ + 1) |
| 53 | 2,4,6-trimethylphenyl-B(OCH2C(CH3)2CH2O) | 232 | 233 (M+ + 1) |
| 54 | 2-CN-C6H4-B(OCH2CH2O) | 173 | 174 (M+ + 1) |
| 55 | 4-NC-C6H4-B(OCH2CH2O) | 173 | 174 (M+ + 1) |
| 56 | 1-oxo-indan-5-yl-Bpin | 258 | 259 (M+ + 1) |
| 57 | 3-methoxy-4-hydroxy-5-formylphenyl-Bpin | 278 | 279 (M+ + 1) |
| 58 | 3,5-dimethylisoxazol-4-yl-B(OCH2CH2O) | 167 | 168 (M+ + 1) |

TABLE 2-continued

NOVEL BORONATES PREPARED BY DIBORON METHODOLOGY

| Compound Number | COMPOUND STRUCTURE | Calc M/Z | Found M/z |
|---|---|---|---|
| 59 | (structure: fluoro-cyano-phenyl 1,3,2-dioxaborolane) | 191 | 192 (M⁺ + 1) |
| 60 | (structure: thiazol-2-yl 1,3,2-dioxaborolane) | 155 | 156 (M⁺ + 1) |
| 61 | (structure: methoxy, NCH₂C substituted phenyl 5,5-dimethyl-1,3,2-dioxaborinane) | 259 | 260 (M⁺ + 1) |
| 62 | (structure: 3-phenoxyphenyl 1,3,2-dioxaborinane) | 254 | 255 (M⁺ + 1) |
| 63 | (structure: thiazol-2-yl pinacol boronate) | 211 | 212 (M⁺ + 1) |
| 64 | (structure: 3-(trimethoxysilyl)phenyl pinacol boronate) | 324 | 325 (M⁺ + 1) |
| 65 | (structure: 4-(trimethoxysilyl)phenyl pinacol boronate) | 324 | 325 (M⁺ + 1) |

The term "linking group" as used herein refers to any chain of atoms linking one aryl group to another. Examples of linking groups include polymer chains, optionally substituted alkylene group and any other suitable divalent group.

The process according to the present invention is applicable to chemistry on solid polymer support or resin bead in the same manner as conventional chemistry is used in combinatorial chemistry and in the preparation of chemical libraries. Thus a suitable organic compound having a halogen or halogen-like substituent at a coupling position which is chemically linked to a polymer surface may be reacted with an arylboron intermediate in the presence of a Group VIII metal catalyst and a suitable base to form a coupled product linked to the surface of the polymer. Excess reagents and by-products may then be washed away from the surface leaving only the reaction product on the surface. The coupled product may then be isolated by appropriate cleavage of the chemical link from the polymer surface. The process is also possible using the alternative strategy of reacting an aromatic ring or an aromatic ring compound having a halogen or halogen-like substituent linked to a polymer surface with a diboron derivative in the presence of a Group VIII metal catalyst and a suitable base to form an arylboron intermediate chemically linked to the polymer surface. This intermediate may then be reacted with an organic compound having a halogen or halogen-like substituent at a coupling position in the presence of a Group VIII metal catalyst and a suitable base to prepare the coupled product chemically linked to the polymer. Excess reactants and by-products may be removed by suitable washing and the coupled product may be isolated by chemically cleaving the link to the polymer.

In accordance with the present invention it is also possible to directly functionalise the surface of a polymer, e.g. polystyrene, with a halogen or halogen-like substituent and then convert this functionalised surface to an arylboron surface by reaction of the functionalised polymer with a diboron derivative in the presence of a Group VIII metal catalyst and a suitable base. The arylboron surface may then be reacted with any suitable organic compound having a halogen or halogen-like substituent. If the aromatic ring compound contains other functional groups, for example carboxylic ester, they may be used as linker groups to further extend the chemical reactions applied to the polymer surface.

It is also possible to prepare polyaryl compounds or other polymers by reaction of aromatic ring compounds having more than one halogen or halogen-like substituent. Such aromatic ring compounds may be reacted with a diboron derivative in the presence of a Group VIII metal catalyst and a suitable base to form an arylboron intermediate having more than one boron functionality. These intermediates may be reacted with aromatic ring compounds or organic compounds having more than one halogen or halogen-like substituent to form a polymer. If the aromatic ring compound has three or more halogen or halogen-like substituents which react with the diboron derivative then it is possible to prepare dendritic molecules in accordance with the process of the present invention.

The aromatic ring compound and the organic compound may be separate molecules or may be linked together such that the arylboron intermediate formed after reaction with the diboron derivative is able to react at a coupling position located elsewhere in the molecule so as to provide for an intramolecular reaction, such as a ring closure reaction. Similarly the process according to the invention allows intramolecular linking to occur between different aromatic rings bearing halogen or halogen-like substituents located at different parts of the molecule. Reaction of one halide substituent with a diboron ester to form an arylboron intermediate allows reaction of that intermediate with the halide substituent on the other ring to thereby link the aromatic rings.

The process according to the invention is also useful for the preparation of reactive intermediates which are capable of taking part in further reactions or rearrangements. These reactive intermediates may be the aryl boron intermediates or the coupled products. The aryl boron intermediates may take part in one or more of the palladium catalysed reactions of aryl boron compounds described by Miyaura and Suzuki in Chem. Rev. 1995, 95 2457–2483.

The process according to the present invention allows the linking of aromatic rings and aromatic ring compounds to organic compounds in mild conditions and avoids the use of expensive, difficult to remove and/or toxic reagents and solvents. In this regard boron and boron compounds are generally non-toxic. The reactions may also be performed in relatively cheap solvents such as methanol and ethanol and, in view of the improved control over the reaction steps, it is envisaged that it would be possible to perform the reactions on an industrial scale. The process also allows the linking of aromatic rings which contain active hydrogen substituents without the need to protect those substituents during the reaction.

The following examples are provided to illustrate some preferred embodiments of the invention. However it is to be understood that the following description is not to supersede the generality of the invention previously described.

EXAMPLES

Example 1

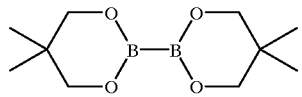

Freshly distilled neopentanediol (9.72 g, 0.093 mol) was placed in a dry 250 ml Schlenk flask, anhydrous diethyl ether (100 ml) added under argon, followed by tetrakis-(dimethylamino)diboron (9.24 g; 0.047 mol). The mixture was stirred magnetically under argon and cooled in ice. A solution of hydrogen chloride in dry diethyl ether (76 ml of 2.46 M, 0.187 mol) added from a pressure-equalising dropping funnel over 1 h and the mixture allowed to warm to room temperature with stirring overnight. The solution was filtered from the copious precipitate through a glass filter tube into a second Schlenk flask and the filtrate evaporated to dryness affording a white solid (2.89 g, 23%) whose nmr indicated it was the product. The residual precipitate was extracted with hot benzene (2×200 ml) and the extracts filtered and evaporated to provide further product (6.36 g, total yield 74%). The combined extracted products were recrystallised from benzene/light petroleum (b.p. 60–80° C.) to afford bis(neopentanediolato)diboron as colourless tetrahedral prisms, m.p. 161–162° C. $^1$H nmr (CDCl$_3$): δ 0.95 (2×CH$_3$) and 3.60 ppm (2×OC$\underline{H}_2$). $^{13}$C nmr (CDCl$_3$): δ 22.1 (2×$\underline{C}$H$_3$); 31.6 (R$_4\underline{C}$) and 71.5 ppm (2×O$\underline{C}$H$_2$). $^{11}$B nmr (CDCl$_3$): δ 27.4 ppm (B—B).

Example 2

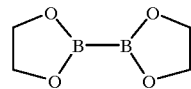

Anhydrous ethylene glycol (9.15 ml, 0.164 mol) was added to tetrakis(dimethylamino)-diboron (16.24 g; 0.0820 mol) in anhydrous diethyl ether (170 ml) contained in a 2-neck 500 ml round bottom flask under nitrogen. The mixture was stirred magnetically under nitrogen and cooled in ice. A solution of hydrogen chloride in dry diethyl ether (115 ml of 2.85 M, 0.328 mol) was added from a pressure-equalising dropping funnel over 1 h and the mixture allowed to warm to room temperature with stirring overnight. The solution was filtered from the copious precipitate by suction filtration through a glass sinter funnel and the filtrate evaporated to dryness affording a white solid (3.12 g) whose nmr indicated it was the product along with some dimethylamine hydrochloride salt. The residual precipitate was extracted with hot benzene (2×200 ml) and the extracts filtered and evaporated to dryness affording a white solid (8.41 g, 72%) whose nmr showed indicated it was the desired product. The first crop (3.12 g) was extracted with hot benzene (60 ml) and the extract filtered and evaporated to dryness affording a white solid (2.23 g) whose nmr showed indicated it was the desired product. The combined extracted products were recrystallised from benzene/light petroleum (b.p. 60–80° C.) to afford bis(ethanediolato)diboron as colourless crystals. Yield 9.90 g (0.0700 mol; 85%). $^1$H nmr (CDCl$_3$, 200 MHZ): δ 4.18 ppm (singlet, OC$\underline{H}_2$). $^{13}$C nmr (CDCl$_3$, 200 MHZ): δ 65.5 ppm (OCH,).

Example 3

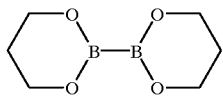

Freshly distilled 1,3-propanediol (10.22 g; 0.134 mol) was added to tetrakis(dimethyl-amino)diboron (13.29 g; 0.0671 mol) in anhydrous ether (200 ml) contained in a 2-neck 500 ml round bottom flask, under nitrogen. The mixture was stirred magnetically under nitrogen and cooled in ice. A solution of hydrogen chloride in dry ether (94.5 ml of 2.85 M, 0.269 mol) added from a pressure-equalising dropping funnel over 1 h and the mixture allowed to warm to room temperature with stirring overnight. The solution was filtered from the copious precipitate by suction filtration through a glass sinter funnel and the filtrate evaporated to dryness to give the product as a colourless solid (9.50 g, 83%). $^1$H nmr (CDCl$_3$, 200 MHZ): δ 1.87 (quintet, 2H, CH$_2$CH$_2$CH$_2$) and 3.93 ppm (triplet, 4H, CH$_2$O). $^{13}$C nmr (CDCl$_3$, MHZ): δ 27.4 (CH$_2$CH$_2$CH$_2$, 1C) and 61.1 ppm (CH$_2$O, 2C).

Example 4

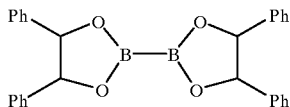

Meso-hydrobenzoin (45.66 g; 0.213 mol) was added to tetrakis(dimethylamino)diboron (21.09 g; 0.107 mol) in anhydrous diethyl ether (500 ml) contained in a 2-neck 1 L round bottom flask under nitrogen. The mixture was stirred magnetically under nitrogen and cooled in ice. A solution of hydrogen chloride in dry diethyl ether (150 ml of 2.85 M, 0.428 mol) was added from a pressure-equalising dropping funnel over 1 h and the mixture allowed to warm to room temperature with stirring overnight. The solution was filtered from the copious precipitate by suction filtration through a glass sinter funnel and the filtrate evaporated to dryness affording a small amount of white solid. The standard workup yielded 33.62 g (0.0754 mol; 71%).

Example 5

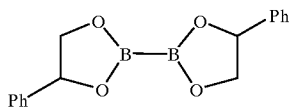

This diboronic acid ester was prepared following the procedure described above for Example 1 using 1-phenyl-1,2-ethanediol instead of neopentanediol. Yield, 73%. $^1$H nmr (CDCl$_3$, 200 MHz): δ 4.04–4.12 (triplet, 2H; 2× HCHCPh), 4.57–4.66 (triplet, 2H; HCHCPh), 5.44–5.52 (triplet, 2H; 2×OCHPh) and 7.28–7.42 ppm (multiplet, 10H; 2×ArH).

Example 6

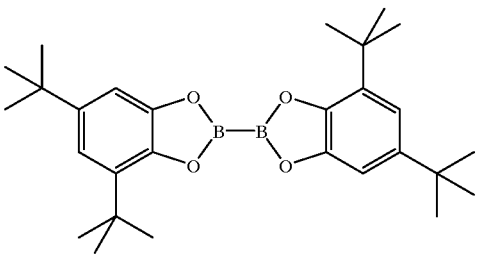

This diboronic ester was prepared following the procedure described above for Example 1 using 3,5di-tert-butylcatechol instead of neopentanediol. Yield, 41%. $^1$H nmr (CDCl$_3$, 200 MHZ): δ 1.21–1.51 (multiplet, 36H; 12×CH$_3$) and 6.82–7.30 ppm (multiplet, 4H; 2×ArH). F.W.: calc for C$_{28}$H$_{40}$B$_2$O$_4$=462.25, found m/z 463 (M+1).

Example 7

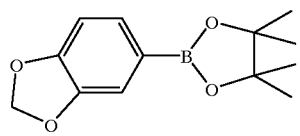

In a Schlenk tube, a solution of the pinacol ester of diboronic acid (0.315 g; 1.24 mmol), 1-iodo-3,4-methylenedioxybenzene (0.252 g; 1.02 mmol), PdCl$_2$(dppf).CH$_2$Cl$_2$ (24 mg; 0.029 mmol) and potassium acetate (0.300 g; 3.06 mmol) in an ethanol-water solvent mixture (6 ml, 95% EtOH:5% H$_2$O) was placed under an atmosphere of nitrogen and heated at 40° C. with stirring. After 2.5 h gc analysis on the reaction mixture showed some decomposition of the diboron compound, 64% unreacted aryl iodide and the formation of the arylboronic acid ester in 36% yield. More diboron compound (173 mg; 0.68 mmol) was added under nitrogen to the reaction mixture and heating at 40° C. continued. After 4 h gc analysis on the reaction mixture showed absence of diboron compound, 28% unreacted aryl iodide and the formation of the arylboronic acid ester in 72% yield.

Additional diboron compound was added to the reaction mixture until gc analysis indicated the reaction had gone to completion. The product was then isolated by pouring the ethanolic reaction mixture into water (10 ml) and extracting into diethyl ether (2×50 ml). The combined ether extracts were dried (MgSO$_4$) and the solvent removed under vacuum to yield the crude product which was then purified by distillation under vacuum (80–120° C./2.5×10$^{-2}$ atm).

$^1$H nmr (CDCl$_3$, 200 MHZ): δ 1.27 (singlet, 12H, C(CH$_3$)$_2$) 5.89 (singlet, 2H, CH$_2$O) and 6.72–7.31 ppm (multiplet, 3H, ArH).

Example 8

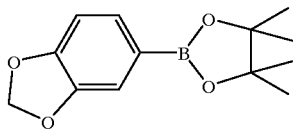

In a Schlenk tube, a solution of the pinacol ester of diboronic acid (0.327 g; 1.29 mmol), 1-bromo-3,4-methylenedioxybenzene (0.211 g; 1.05 mmol), PdCl$_2$(dppf).CH$_2$Cl$_2$ (24 mg; 0.029 mmol) and potassium acetate (0.302 g; 3.08 mmol) in an ethanol-water solvent mixture (6 ml; 95% EtOH:5% H$_2$O) was placed under an atmosphere of nitrogen and heated at 60° C. with stirring. After 2.5 h gc analysis on the reaction mixture showed absence of the diboron compound, 32% unreacted aryl bromide and the formation of the arylboronic acid ester (identified by gc retention time) in 68% yield.

Examples 7 and 8 demonstrate that although additional quantities of diboron derivatives may be required, arylboronic acid esters can be formed from aryl iodides and aryl bromides in aqueous ethanol.

Example 9

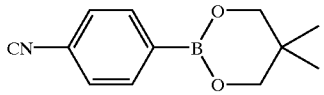

In a Schlenk tube, a solution of bis(neopentanediolato)diboron (0.374 g; 1.66 mmol), 4-iodobenzonitrile (0.250 g; 1.09 mmol), PdCl$_2$(dppf).CH$_2$Cl$_2$ (27 mg; 0.033 mmol) and potassium acetate (0.321 g; 3.27 mmol) in dry methanol (6 ml) was placed under an atmosphere of nitrogen and stirred at room temperature for 3 days. The excess diboron compound, arylboronic acid ester (94%) and biaryl compound (3%) gave rise to the three peaks in the gc, arylboronic acid ester: biaryl=32.0. The reaction mixture was poured into water (20 ml) and extracted into diethyl ether (1×75 ml, 1×50 ml). The combined ether extracts were washed (water; 2×50 ml), dried (MgSO$_4$) and the solvent removed under vacuum to give a pale brown solid. Purification by distillation under vacuum afforded a white solid (80–100° C/2.5×10$^{-2}$atm) Yield 0.17 g (0.79 mmol; 73%). $^1$H nmr(CDCl$_3$, 200 MHZ): δ 0.95 (singlet, 6H, C$\underline{H}_3$), 3.71 (singlet, 4H, C$\underline{H}_2$O) and 7.52–7.82 ppm (multiplet, 4H, Ar $\underline{H}$). F.W. calc for C$_{12}$H$_{14}$BNO$_2$, 215.06; found (CI+mass spectrum): m/z 216 (M+1), 244 (M+29) and 256 (M+41).

Example 10

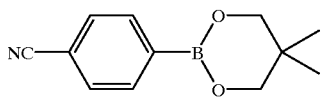

In a Schlenk tube, a solution of bis(neopentanediolato)diboron (0.370 g; 1.64 mmol), 4-iodobenzonitrile (0.250 g; 1.09 mmol), PdCl$_2$(dppf).CH$_2$Cl$_2$ (27 mg; 0.033 mmol) and potassium acetate (0.325 g; 3.29 mmol) in dry isopropyl alcohol (7 ml) was placed under an atmosphere of nitrogen and heated at 60° C. with stirring. After 24 h the arylboronic acid ester (93%) and the symmetrical biaryl compound (7%) gave rise to the two peaks observed in the gc, arylboronic acid ester:biaryl 13.3. The reaction mixture was filtered collecting a grey solid which was taken up in chloroform (25 ml). Some insoluble material was removed by suction filtration and the filtrate taken to dryness under vacuum to give a red-brown solid. Purification of this material by distillation under vacuum afforded a white solid at 80–100° C./2.9×10$^{-2}$ atm.

$^1$H nmr (CDCl$_3$, 200 MHZ): as in Example 9.

Although the gc analysis indicated that the diboron compound had been exhausted, some of this material was recovered during distillation of the crude product. Accordingly % yields determined by gc have not been standardized.

Examples 9 and 10 demonstrate that the neopentanediol ester of diboronic acid can also be used to form arylboronic acid esters, in methanol or isopropyl alcohol.

Example 11

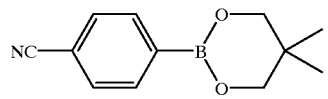

In a Schlenk tube, a solution of the pinacol ester of diboronic acid (0. 359 g; 1.41 mmol), 4-iodobenzonitrile (0.251 g; 1.10 mmol), PdCl$_2$(dppf).CH$_2$Cl$_2$ (27 mg; 0.033 mmol) and potassium acetate (0.118 g; 1.20 mmol) in dry methanol (6 ml) was placed under an atmosphere of nitrogen and heated at 60° C. After 18 h gc analysis shows the excess diboron compound, 17% unreacted aryl iodide, 59% arylboronic acid ester as well as 24% of the symmetrical biaryl compound. Arylboronic acid ester:Biaryl =2.5.

Examples 9 and 11 demonstrate that the bis(neopentanediolato)diboron compound, when reacted with 4-iodobenzonitrile, produces less biaryl product than a similar reaction with the pinacol ester of diboronic acid.

Example 12

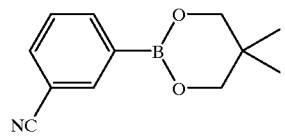

In a Schlenk tube, a solution of bis(neopentanediolato)diboron (0.321 g; 1.42 mmol), 3-iodobenzonitrile (0.251 g; 1.10 mmol), PdCl$_2$(dppf).CH Cl 2(28 mg; 0.034 mmol) and potassium acetate (0.118 g; 1.20 mmol) in dry methanol (6.5 ml) was placed under an atmosphere of nitrogen and heated at 60° C. After 18 h the arylboronic acid ester (83%) and the symmetrical biaryl compound (17%) gave rise to the two peaks observed in the gc.

Example 13

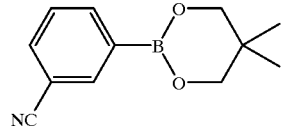

In a Schlenk tube, a solution of the pinacol ester of diboronic acid (0.363 g; 1.43 mmol), 3-iodobenzonitrile (0.250 g; 1.09 mmol), PdCl$_2$(dppf).CH$_2$Cl$_2$ (27 mg; 0.033 mmol) and potassium acetate (0.120 g; 1.22 mmol) in dry methanol (7 ml) was placed under an atmosphere of nitrogen and heated at 60° C. After 18 h gc analysis shows the excess diboron compound, 9% unreacted aryl iodide, 73% arylboronic acid ester as well as 18% of the symmetrical biaryl compound.

Example 14

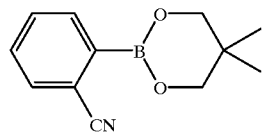

In a Schlenk tube, a solution of bis(neopentanediolato) diboron (0.322 g; 1.43 mmol), 2-iodobenzonitrile (0.250 g; 1.09 mmol), PdCl$_2$(dppf).CH$_2$Cl$_2$ (27 mg; 0.033 mmol) and potassium acetate (0.120 g; 1.22 mmol) in dry methanol (6.5 ml) was placed under an atmosphere of nitrogen and heated at 60° C. After 18 h gc analysis shows the absence of diboron compound, some unreacted aryl halide and some product formation. More diboron compound (0.167 g; 0.739 mmol) was added and heating at 60° C. was continued. After 5 h gc analysis shows excess diboron compound, 30% unreacted aryl iodide, 66% arylboronic acid ester as well as 4% of the symmetrical biaryl compound. Arylboronic acid ester:Biaryl=17.8.

Example 15

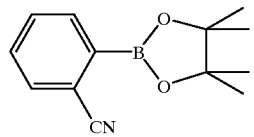

In a Schlenk tube, a solution of the pinacol ester of diboronic acid (0.360 g; 1.42 mmol), 2-iodobenzonitrile (0.250 g; 1.09 mmol), PdCl$_2$(dppf).CH Cl 2(27 mg; 0.033 mmol) and potassium acetate (0.120 g; 1.22 mmol) in dry methanol (7 ml) was placed under an atmosphere of nitrogen and heated at 60° C. After 18 h gc analysis shows the excess diboron compound, 30% unreacted aryl iodide, 31% arylboronic acid ester as well as 39% of the symmetrical biaryl compound. Arylboronic acid ester:Biaryl=0.80.

Examples 14 and 15 demonstrate that the bis (neopentanediolato)diboron compound, when reacted with 2-iodobenzonitrile, produces less biaryl product than a similar reaction with the pinacol ester of diboronic acid, indicating that choice of diboron ester derivative may allow control over the reaction products formed.

Example 16

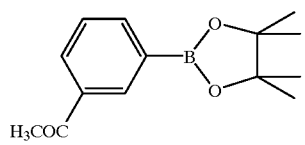

In a Schlenk tube, a solution of the pinacol ester of diboronic acid (0.362 g; 1.43 mmol), 3-iodoacetophenone (0.268 g; 1.09 mmol), PdCl$_2$(dppf).CH$_2$Cl$_2$ (28 mg; 0.034 mmol) and potassium acetate (0.1 18g; 1.20 mmol) in dry methanol (6.5 ml) was placed under an atmosphere of nitrogen and heated at 60° C. After 18 h gc analysis shows 14% unreacted aryl iodide, 79% arylboronic acid ester as well as 7% of the symmetrical biaryl compound. Arylboronic acid ester:Biaryl=12.1.

Example 17

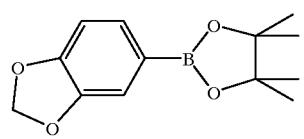

In a Schlenk tube, a solution of the pinacol ester of diboronic acid (0.323 g; 1.27 mmol), 1-iodo-3,4-methylenedioxybenzene (0.241 g; 0.972 mmol), PdCl$_2$(dppf).CH$_2$Cl$_2$ (24 mg; 0.029 mmol) and potassium benzoate (0.469 g; 2.93 mmol) in dry methanol (6.5 ml) was placed under an atmosphere of nitrogen and heated at 60° C. After 18 h gc analysis shows the reaction to have gone to completion to form the arylboronic acid ester.

Example 18

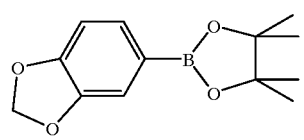

In a Schlenk tube, a solution of the pinacol ester of diboronic acid (0.347 g; 1.37 mmol), 1-iodo-3,4-methylenedioxybenzene (0.259 g; 1.04 mmol), PdCl$_2$(dppf). CH$_2$Cl$_2$ (26 mg; 0.032 mmol) and sodium fluoroacetate (0.317 g; 3.17 mmol) in dry methanol (7 ml) was placed under an atmosphere of nitrogen and heated at 60° C. After 18 h gc analysis shows 53% unreacted aryl iodide and 47% arylboronic acid ester.

Example 19

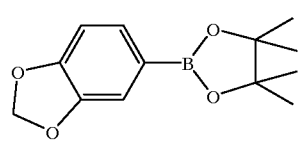

In a Schlenk tube, a solution of the pinacol ester of diboronic acid (0.322 g; 1.27 mmol), 1-iodo-3,4-methylenedioxybenzene (0.242 g; 0.976 mmol), PdCl$_2$ (dppf).CH$_2$Cl$_2$ (24 mg; 0.029 mmol) and sodium trifluoroacetate (0.403 g; 2.96 mmol) in dry methanol (7 ml) was placed under an atmosphere of nitrogen and heated at 60° C. After 18 h gc analysis shows 82% unreacted aryl iodide, 15% arylboronic acid ester and 3% symmetrical biaryl.

Examples 17, 18 and 19 show that using other bases such as potassium benzoate, sodium fluoroacetate or sodium trifluoracetate in these reactions, instead of potassium acetate, also leads to the formation of the desired arylboronic acid ester.

Example 20

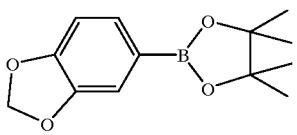

In a Schlenk tube, a solution of the pinacol ester of diboronic acid (0.284 g; 1.12 mmol), 1-iodo-3,4-methylenedioxybenzene (0.244 g; 0.984 mmol), potassium acetate (0.316 g; 3.22 mmol) and approx. 0.18% palladium on porous glass (1.953 g; 0.0336 mmol) in dry methanol (8 ml) at 60° C. After 18 h gc analysis shows no diboron compound starting material, 47.1% unreacted aryl iodide, 49.7% arylboronic acid ester and 3.2% symmetrical biaryl.

Example 21

In a reaction tube, a solution of the pinacol ester of diboronic acid (1.386 g; 5.46 mmol), bromopolystyrene (1.2–1.3 mmol Br/g resin, 2.001 g; 2.50 mmol), potassium acetate (0.751 g; 7.65 mmol) and $PdCl_2(dppf).CH_2Cl_2$ (61 mg; 0.075 mmol) in dry dioxane (40 ml) was placed under an atmosphere of nitrogen and heated at 80° C. After 21 h the reaction mixture was cooled to room temperature and the brown-grey resin collected by vacuum filtration. Tetrahydrofuran (40 ml) was added to the product and the mixture heated at 70° C. for 30 min. before being filtered hot. This washing was repeated till no trace of the pinacol ester of diboronic acid was detected in the washing by gc. To remove all traces of palladium the resin was washed 5 times with a solution of 0.5% sodium dimethyldithiocarbamate and 0.5% diisopropylamine in AR dimethylformamide, using an ultrasonic bath. The resin was washed several times with tetrahydrofuran followed by several washes with a dioxane-water mixture before being dried under vacuum (50° C./28 in Hg) overnight.

Example 22

Aryl Borate Formation Using Phenyl Triflate

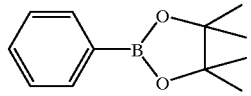

In a Schlenk tube, a solution of the pinacol ester of diboronic acid (0.308 g; 1.21 mmol), phenyl triflate (0.249 g; 1.10 mmol), potassium acetate (0.330 g; 3.36 mmol) and $PdCl_2(dppf).CH_2Cl_2$ (27 mg; 0.033 mmol) in dry dimethylsulphoxide (6 ml) was placed under an atmosphere of nitrogen and heated at 80° C. After 18 h gc analysis shows the reaction to have gone to completion. The reaction mixture was poured into water (20 ml) and extracted into diethyl ether (1×75 ml, 1×50 ml). The combined ether extracts were washed (water; 2×50 ml), dried ($MgSO_4$) and the solvent removed under vacuum to give a green oil. Purification by column chromatography (silica gel 60) eluting with chloroform:petroleum spirit 40–60° (1:1) solvent mixture afforded a colourless oil.

$^1$H nmr ($CDCl_3$, 200 MHZ): δ 1.35 (singlet; 12H, 4×$CH_3$) and 7.26–7.84 ppm (multiplet; 5H, Ar$\underline{H}$). F.W.: calc for $C_{12}H_{17}BO_2$, 204.08; found (CI/MS) 204 ($M^+$).

Example 23

Hydrolysis of the Pinacol Ester of Phenylboronic Acid

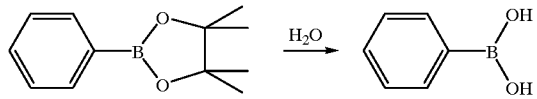

A methanolic solution of the pinacol ester of phenylboronic acid (ArB(pin)) was analysed by HPLC (Waters 600E) using a Zorbax column (ODS) under the following conditions: λ=230 nm, 2 ml/min., 20% $CH_3CN$: 80% $H_2O$ (initial) to 80% $CH_3CN$: 20% $H_2O$ (changed linearly from 9–17 min.). Peaks were detected at 5.9 min. and 14.9 min., the former assigned to phenylboronic acid (by spiking the solution with an authentic sample) and the later to ArB(pin). The ratio [area ArB(OH)$_2$]/[area ArB(pin)]=0.074.

To another sample of the initial methanolic solution was added some water and after several hours HPLC analysis showed peaks at 5.6 and 14.7 minutes with an area ratio of 0.44. This indicates hydrolysis of the pinacol ester of phenylboronic acid to phenylboronic acid on exposure to water.

Example 24

Hydrolysis of the Neopentanediol Ester of Phenylboronic Acid

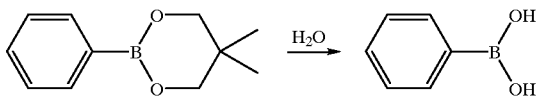

A methanolic solution of the neopentanediol ester of phenylboronic acid was analysed by HPLC (Waters 600E) using a Zorbax column (ODS) under the following conditions: λ=230 nm, 2 ml/min., 20% $CH_3CN$:80% $H_2O$ (initial) to 80% $CH_3CN$:20% $H_2O$ (changed linearly from 9–17 min.). A single peak was detected at 5.8 minutes. This peak was confirmed to be due to phenylboronic acid by spiking the solution with an authentic sample.

A sample was also collected by semi-preparative HPLC and found to be phenylboronic acid.

This indicates the ready hydrolysis of the neopentanediol ester of phenylboronic acid to phenylboronic acid on exposure to water.

Examples 23 and 24 show that although hydrolysis of the phenyl boronates of pinacol and neopentanediol in water does occur, the phenyl boronate of pinacol is more stable.

Example 25

In a Schlenk tube, a solution of the pinacol ester of diboronic acid (0.513; 2.02 mmol), 1-bromo-3,4-methylenedioxybenzene (0.250 g; 1.24 mmol), potassium acetate (0.371 g; 3.78 mmol), $PdCl_2(dppf).CH_2Cl_2$ (33 mg; 0.040 mmol) and internal standard biphenyl (0.188 g; 1.22 mmol) in dry methanol (6 ml) was placed under an atmosphere of nitrogen and heated at 60° C. After 18 h gc analysis shows the reaction to have gone to completion and the ratio [diboron compound]/[internal standard]=0.36. Water (2.5 ml) was added and heating at 60° C. was continued. After 5 h no diboron compound is detected by gc.

This example shows that excess pinacol ester of diboronic acid can be decomposed by hydrolysis by addition of water to the reaction solution. This procedure lends itself to the synthesis of unsymmetrical biaryls by minimising the formation of the symmetrical species.

Example 26

Reaction of Aryl Chloride

Boronic acid ester from p-chloronitrobenzene

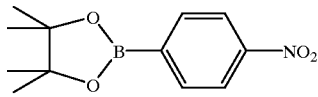

p-Chloronitrobenzene (2 mmol) was heated at 100° C. in DMSO for 24 h with 1.1 mmol of the pinacol ester of diboronic acid, 3 mmol $Cs_2CO_3$ and 24 mg $PdCl_2$(dppf).$CH_2Cl_2$. The reaction solution was extracted with $CH_2Cl_2$/water. The gc of the $CH_2Cl_2$ solution had peaks identified by gc/ms for the ester (m/z 249; M+1) and at longer retention time, dinitrobiphenyl (m/z 245; M+1).

When $PdCl_2[(P(C_6H_{11})_3)_2]$ or $PdCl_2[(C_6H_5)_2P(CH_2)_4P(C_6H_5)_2]$ was used as catalyst, all the boronic acid ester that had formed coupled with p-chloronitrobenzene to form the dinitrobiphenyl.

Example 27

Use of Ni as the Catalyst Element

The pinacol ester of diboronic acid (1.09 mmol), 1-iodo-3,4-methylenedioxybenzene (0.99 mmol), 25 mg $NiCl_2$(dppf) prepared by the method of A. W. Rudie et al., Inorg. Chem. 1978, 17, 2859, and potassium acetate (3.2 mmol) were stirred in DMSO (5 ml) at 75° C. for 40 h. The ether solution obtained after ether/water extraction of the reaction solution gave only one peak in the gc at a retention time longer than that of the pinacol ester of diboronic acid. The peak was identified by the retention time to be due to the pinacol ester 3,4-methylenedioxyphenylboronic acid.

Example 28

Coupling of Arylsulfonic Acids. Synthesis of

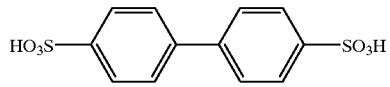

The sodium salt of p-bromophenylsulfonic acid (2 mmol) and the pinacol ester of diboronic acid (1.1 mmol) were reacted in 5 mls DMSO at 80° C. for 21.5 h in the presence of 1 g $Cs_2CO_3$ and 26 mg $PdCl_2$(dppf).$CH_2Cl_2$. The DMSO was removed under reduced pressure and the remainder taken up in water and passed down a Amberlite IR-120 [H+ form] column to remove the inorganic cations and carbonate. The acid was obtained as a solid on freeze drying the aqueous solution after the impurities had been removed with the aid of THF and ethanol. $^1$H nmr in $D_2O$ gave an AB type quartet entered at 7.68 ppm, J=8.40 Hz. The mass spectrum (APCI, negative ion) gave peaks at m/z 313 (M−1) and 233 (M−$SO_3H$).

Example 29

Pinacol Ester of Phenyltrimethoxysilylboronic Acid

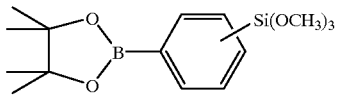

In a reaction tube 0.587 g (6 mmol) potassium acetate was dried at 150° C., $3\times10^{-7}$ mmHg for 3 h. Then, under Ar, $PdCl_2$(dppf).$CH_2Cl_2$ (49 mg), pinacol ester of diboronic acid (540 mg, 2.13 mmol), 0.35 ml (2.06 mmol) of bromophenyltrimethoxy-silane (mixture of isomers, Gelest Inc.) and 4 mls dry DMSO were added. The tube was warmed with stirring to 80° C. for 21 h. After removal of the DMSO under high vacuum near room temp., the temperature of the Kugelrohr was increased to 30 and then 50° C. to remove other volatile impurities. The product was distilled as a colourless liquid at 70–75° C., $3\times10^{-7}$ mm Hg. The $^1$H nmr in $CDCl_3$; 1.35 ppm(s, 12H, $CCH_3$); 3.61 ppm, 3.62 ppm (peaks near equal area, 9H, $OCH_3$), 7.35–8.15 ppm (multiplets, 4H). The aromatic protons indicate the presence of the para-substituted compound (AB type quartet; 7.64, 7.68, 7.81, 7.85 ppm) and the meta-substituted compound (7.36 (tr), 7.75 (d), 7.90 (d), 8.10 (s)). The gc of the material gave two peaks of near equal area and both compounds represented by these peaks gave a parent ion mass of 325 (M+1) in the gc/ms.

Example 30

Synthesis of 5,5'-Dimethyl-2,2'-Bipyridine

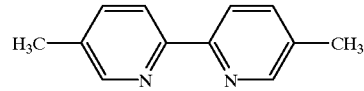

The coupling of 2-bromo-5-methylpyridine can be readily carried out with bases such as $Cs_2CO_3$ or $C_6H_5OP(O)(ONa)_2$.$H_2O$ in ethanol. Pyridine can also be used. Examples are given with $PdCl_2$(dppf).$CH_2Cl_2$ or palladium acetate as catalyst. Reaction temperatures used varied from 50° C. to 80° C.

(a) Placed 330 mg (1.92 mmol) of 2-bromo-5-methylpyridine in a reaction tube together with 274 mg (1.08 mmol) of the pinacol ester of diboronic acid, 26 mg $PdCl_2$(dppf).$CH_2Cl_2$ and 0.97 g $Cs_2CO_3$. After addition of 6 ml dry ethanol, the reaction was warmed to 80!C. for several days (reaction time not optimized). The gc of the extracted (ether/water) reaction solution had 2 peaks, a small one being the starting bromopyridine and the large peak shown to be by gc/ms (m/z 185; M+1) the product 5,5'-dimethyl-2,2'-bipyridine.

(b) Placed 86 mg (0.50 mmol) of 2-bromo-5-methylpyridine in a reaction tube together with 148 mg (0.58 mmol) of the pinacol ester of diboronic acid, 15 mg $PdCl_2$(dppf).$CH_2Cl_2$ and 369 mg of $C_6H_7OP(O)(ONa)_2$.$H_2O$. After addition of 4 ml. pyridine the mixture was warmed to 60!C. for 2 h and then to 80° C. for 15.5 h.

Only one peak was observed in the gc of the ether/water extracted reaction product and at a residence time corresponding to that found for the 5,5'-dimethyl-2,2'-bipyridine.

(c) Placed 332 mg (1.93 mmol) of 2-bromo-5-methylpyridine in a reaction tube together with 270 mg (1.06 mmol) of the pinacol ester of diboronic acid, 25 mg Pd(OAc)$_2$ and 1.11 g (3.1 mmol) Cs$_2$CO$_3$. After addition of 6 ml ethanol the mixture was warmed to 60° C. After 3 h the gc of the ether/water extracted reaction solution gave only two peaks, a weak one of retention time characteristic of the starting bromopyridine and the other peak had a retention time characteristic of the 5,5'-dimethyl-2,2'-bipyridine.

(d) Placed 86 mg (0.50 mmol) of 2-bromo-5-methylpyridine in a reaction tube together with 151 mg (0.59 mmol) of the pinacol ester of diboronic acid, 13.5 mg Pd(OAc)$_2$ and 360 mg (1.52 mmol) of C$_6$H$_5$OP(O)(ONa)$_2$ H$_2$O. After addition of 3 ml ethanol the mixture was warmed to 60° C. After 1.33 h the gc of an aliquot of the reaction mixture (extracted with ether/water) indicated the formation of the 5,5'-dimethyl-2,2'-bipyridine. The reaction was left for 90 h at 60° C. after which only 5,5'-dimethyl-2,2'-bipyridine was detected in the gc of the ether solution of an ether/water extracted sample of the reaction solution gave only two peaks, a weak one of retention time characteristic of the starting bromopyridine and the other peak had a retention time characteristic of the 5,5'-dimethyl-2,2'-bipyridine.

Example 31

Synthesis of 3,3'-Dimethyl-2,2'-bipyridine

This example shows that 2-bromo-3-methylpyridine can be coupled in the presence of a weak base, KOAc and Pd(OAc)$_2$.

Placed 172 mg(1.0 mmol) of 2-bromo-3-methylpyridine in a reaction tube together with 281 mg (1.11 mmol) of the pinacol ester of diboronic acid, 22.5 mg Pd(OAc)$_2$ and 300 mg (3.06 mmol) of KOAc After addition of 5 ml ethanol the mixture was warmed to 80° C. After 6 h the gc of an aliquot of the reaction mixture (extracted with ether/water) indicated the formation of the 3,3'-dimethyl-2,2'-bipyridine. The reaction was left for 65 h at 80° C. after which the only peaks detected in the gc, of the ether solution of an ether/water extracted sample of the reaction solution, were 3,3'-dimethyl-2,2'-bipyridine (gc/ms, m/z 185, M+1) and the pinacol ester of diboronic acid.

Example 32

Synthesis of 2,2'-Bipyridine

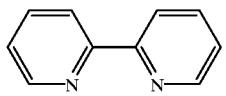

Placed 14.9 mg Pd(OAc)$_2$ (0.0665 mmol) and 72 mg P(o-CH$_3$OC$_6$H$_4$)$_3$ (0.204 mmol) in a reaction tube and dissolved the compounds in 2 ml DMSO at 60° C. for 10 mins. to form palladium phosphine complex. A dark red solution resulted. Then added 258 mg CsF (1.70 mmol), 144 mg of the pinacol ester of diboronic acid, 105 mg 2-iodopyridine (0.51 mmol) and a further 2 ml DMSO. The reaction mixture was warmed to 80° C. for 16 h. The gc of the ether solution of the ether/water extracted reaction solution showed that the reagents had been exhausted and the main peaks besides that of the phosphine were 2,2'-bipyridine (gc/ms; m/z 157, M+1) and o-anisylboronic acid pinacol ester (gc/ms, m/z 235, M+1). 2,2'-bipyridine is also formed when HCOOK is used as base.

When the reaction is carried out (80° C., 16 h) using tri-p-tolylphosphine (68 mg), Pd(OAc), (14 mg), 145 mg (0.57 mmol) of the pinacol ester of diboronic acid, 118 mg 2-iodopyridine (0.58 mmol) and 513 mg (1.45 mmol) Cs$_2$CO$_3$ in 4 ml DMSO, the gc of the ether solution of an ether/water extracted sample of the reaction solution indicated the complete exhaustion of the diboron ester and bromopyridine species and the formation of 2,2'-bipyridine. This reaction can also be carried out using tris-2,4,6-trimethoxyphenyl-phosphine instead of the tri-p-tolylphosphine. The product was identified by gc/ms (m/z 157, M+1). An adjacent peak (m/z 169, M+1) was assigned to the phosphine derived species, 1,3,5-trimethoxybenzene.

Example 33

A solution of 1-bromo-3,4-methylenedioxybenzene (0.20 g; 0.99 mmol), the pinacol ester of diboronic acid (0.56 g; 2.2 mmol), disodium phenyl phosphate (0.47 g; 2.2 mmol), PdCl$_2$(dppf). CHC$_2$Cl$_2$ (25 mg; 0.031 mmol) and internal standard biphenyl (0.15 g; 0.97 mmol) in methanol (5 ml) was heated between 30 and 50° C. till no aryl bromide was detected by gc analysis. N-Chlorosuccinimide (0.27 g; 2.0 mmol) was added and the reaction mixture stirred at room temperature. After 1 h gc analysis shows no diboron compound.

Example 34

In a Schlenk tube, a solution of the pinacol ester of diboronic acid (2.02 g; 7.95 mmol), 2-iodonitrobenzene (0.981 g; 3.94 mmol), PdCl$_2$(dppf).CH$_2$Cl$_2$ (97 mg; 0.12 mmol) and potassium acetate (1. 19 g; 12.1 mmol) in dry DMSO (20 ml) was placed under an atmosphere of nitrogen and heated at 80° C. with stirring. After 5 h gc analysis showed aryl borate as the major product along with diboron compound and small amounts of unreacted aryl iodide, biaryl and evidence of some reduction of the aryl borate to the pinacol ester of 2-aminophenylboronic acid. The reaction mixture was poured into water (40 ml) and extracted into diethyl ether (3×100 ml). Each extract was washed with water (30 ml) and dried over MgSO$_4$. The combined extracts were purified on silica gel 60 eluting with a petroleum spirit 60–80°:ethyl acetate (80:20) solvent mixture. One of the fractions collected, which contained unreacted diboron compound, unreacted aryl iodide, the pinacol ester of 2-nitrophenylboronic acid and the pinacol ester of 2-aminophenylboronic acid was taken to dryness under vacuum before adding a solution of dimethyldioxirane in acetone. After stirring at room temperature for 3 h gc analysis shows only the pinacol ester of 2-nitrophenylboronic acid and a small amount of unreacted aryl iodide.

Examples 33 and 34 show that N-chlorosuccinimide and dimethyldioxirane can decompose the excess pinacol ester of diboronic acid in the presence of an arylboronic acid ester.

Example 35

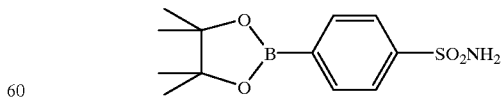

470 mg (1.99 mmol) of 4-bromobenzenesulfonamide were placed in a reaction tube together with 560 mg (2.0 mmol) of the pinacol ester of diboronic acid, 50.8 mg PdCl$_2$(dppf).CH$_2$Cl$_2$ and 600 mg (6.12 mmol) of potassium acetate. After addition of 6 ml DMSO the mixture was warmed to 80° C. for 6 h. An aliquot of the reaction mixture was then extracted with CH$_2$Cl$_2$/water. The gc of the CH$_2$Cl$_2$ solution showed that all the 4-bromo-benzenesulfonamide had been consumed and only a little of the diboron species remained. The product arylboronic acid ester was the only strong peak (gc/ms, M/z 284, M+1) observed. No evidence of a biaryl species was found.

Example 36

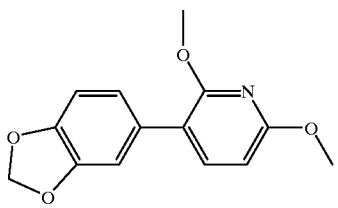

The pinacol ester of diboronic acid (0.154g; 0.607 mmol), 1-iodo-3,4-methylenedioxybenzene (0.268g, 1.08 mmol), 24mg PdCl$_2$(dppf).CH$_2$Cl$_2$ and 0.361g (1.53 mmol) C$_6$H$_5$OPO$_3$Na$_2$.H$_2$O were stirred in methanol (3 ml) at 25° C. for 17.5 h. 90% of the diboron pinacol ester had reacted. After reaction for a further 2 h at 40° C. there was no evidence for any diboron pinacol ester and very little dimer species in the reaction solution even though the iodide was present in 100% excess. After addition of more diboron pinacol ester (0.1075g, 0.408 mmol), (to a total of 1.02 mmol. compared to 1.08 mmol for the iodide) and heating at 40°C. for 17.5 h, a little of the diboron pinacol ester and iodide was still left in the reaction solution. On addition of 0.96 g Cs$_2$CO$_3$ and 0.5 ml H$_2$O and warming to 40° C. for 18.5 h the reaction medium contained arylboron pinacol ester and a trace of dimer. A little of the iodide had been dehalogenated. Treatment of this solution with 3-iodo-2,6-dimethoxypyridine at 40° C. for 4 h led to ca 25% conversion to the mixed diaryl. After a further 68 h reaction at 40° C. all the arylboronic acid ester had reacted. By gc, the product contained two constituents, the minor one was (by gcms) shown to be excess 3-iodo-2,6-dimethoxypyridine and the main one the unsymmetrical diaryl. The ratio of unsymmetrical to symmetric diaryl as judged from the gc (fid detection) was 96:4. The ratio in favour of the unsymmetric diaryl would be further increased by not using excess of the initial halide and optimising reaction times and temperatures.

This example demonstrates that very little of the symmetric diaryl is formed alongside the arylboron ester using the disodium salt of phenylphosphate as base and methanol as solvent, even when the iodide is present in large excess.

Example 37

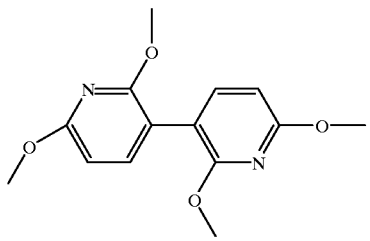

The pinacol ester of diboronic acid (0.282g; 1.11 mmol), 3-iodo-2,6-dimethoxypyridine (0.532g, 2.0 mmol), 24.5 mg PdCl$_2$(dppf).CH$_2$Cl$_2$ and 0.974g (2.99 mmol) Cs$_2$CO$_3$ were stirred in ethanol (6 ml) at 400° C. On testing the reaction (gc) after 20 h no trace of reactants or intermediates was found. The gc of the reaction solution, after washing an aliquot dissolved in ether with water, had only one peak (dimethoxypyridine) other than the strong peak due to the diaryl. 0.24 g of crude material was isolated after removal of the ethanol, extraction of an ether solution of the product with water, drying (MgSO$_4$) and removal of the diethylether under vacuum. The reaction conditions (time/temperature) were not optimised.

This reaction demonstrates the utility of ethanol in the formation of symmetric diaryls. The reaction was carried out at 40° C., but lower temperatures could be employed.

Example 38

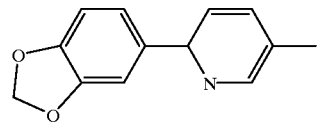

The pinacol ester of diboronic acid (0.363g; 1.43 mmol), 1-iodo-3,4-methylenedioxybenzene (0.310 g, 1.25 mmol), 25 mg PdCl$_2$(dppf).CH$_2$Cl$_2$ and 0.365g (3.72 mmol) of KOAc were stirred in ethanol (8 ml) at 50° C. for 17 h. The excess diboron compound and arylboronic ester give rise to the two peaks observed in the gc. Cs$_2$CO$_3$ (1.3 g, 4.0 mmol) (but no water) was then added, together with 2-bromo-5-methylpyridine (0.24 g, 1.4 mmol), and the reaction heated at 80° C. for a further 22.5 h. The mixed diaryl is the major product together with unreacted 2-bromo-5-methylpyridine and some arylboronic acid ester.

This example demonstrates that certain aryl halides, which do not readily form the arylboronic esters under chosen catalytic conditions, can be coupled with different aryl halides to form the unsymmetrical diaryl, without the water/base decomposition of the excess pinacol ester of diboronic acid before addition of the second aryl halide.

Example 39

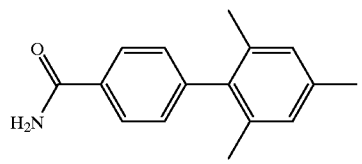

Macro crowns supplied by Chiron Mimotopes Pty Ltd as the Fmoc-protected Rink handle crown were deprotected and converted to 4-iodobenzoyl-Rink handle crowns by standard procedures. The crowns were then reacted in the standard deep well plate with reagents as appropriate to convert them to the boron deriviative and then with aryl iodide to form the bi-aryl. The following solutions were prepared:

a) Pinacol ester of diboronic acid (107 mg) in dimethylsulfoxide (3.5 ml) (0.12 M)
b) Catalyst PdCl$_2$(dppf) (10 mg) in dimethylsulfoxide (1 ml) (0.012 M)
c) Sodium diethyldithiocarbamate (0.5 g) and diisopropylethylamine (0.5g) in dimethylformamide (100 ml)

d) Iodo-2,4,6-trimethylbenzene (24.6 mg) in DMSO (1 ml) (0.1 M)

e) Palladium acetate (0.22 g) in DMSO (10 ml) (10.1 M)

f) Triphenylphosphine (0.42 g) in DMSO (10 ml) (0.0.16 M)

g) Potassium carbonate (4.14 molar; half-saturated) in water.

Typically, to a single well were added solution a) (500 μl) followed by solution b) (100 μl)f and potassium acetate (18 mg approx), the iodobenzoyl crown added and the tube sealed under nitrogen. The reactants were sonicated for 5 min then heated overnight to 80° in an oven containing a nitrogen atmosphere. The tube was cooled, the crown removed and washed by immersion for 5 min successively in DMF, Solution c), DMF, methanol and dichloromethane and then air dried. In a fresh well were then placed solution d) (500 μl), solution e) (20 μl), solution f) (50 μl) and solution g) (37 μl) and the mixture sonicated briefly. The boronated crown prepared above was added, the tube sealed under nitrogen, and the reactants returned to the oven at 80° in a nitrogen atmosphere for 20 h.

The tube was cooled, the crown removed and washed by immersion as above and air dried. The product was then cleaved from the crown by immersion in trifluoroacetic acid (600 μl) in a titre tube and the acid evaporated under a nitrogen stream. The product residue was analysed by hplc (81% pure) and mass spectrometry (Found: m/z 240.2; calc for $C_{16}H_{17}NO_2$, m/z+1=240.1).

This example demonstrates performance of the reaction on a polymer support.

Example 40

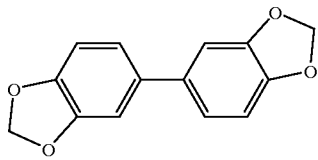

A solution of the pinacol ester of diboronic acid (0.260g; 1 mmol), 1-Bromo-3,4-(methylenedioxy)benzene (0.400 g; 2 mmol), 10% Pd on Carbon (80 mg) and $Cs_2CO_3$ (1.2 g; 3.7 mmol) in methanol (10 ml) was placed under nitrogen and heated at 55° C. with stirring. After 16 hrs, gc analysis of the reaction mixture indicated the formation of the product as the major constituent (83.5%), with the starting 1-bromo-3, 4-(methylenedioxy)benzene accounting for the remainder (16.5%).

This example demonstrates that palladium on a solid support (carbon) can be used as a catalyst.

Example 41

Formation of

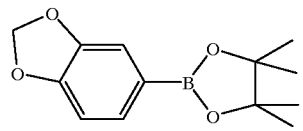

291 mgs (1.14 mmol) of bis(pinacolato)diboron, 25 mg of $PdCl_2(dppt).CH_2Cl_2$ and 211 mg (1.53 mmol) $K_2CO_3$, 200 mg (1.0 mmol) 1-bromo-3,4-methylenedioxybenzene were placed in a reaction tube under nitrogen. After addition of 5 ml dry ethanol, the crimson coloured reaction solution was warmed to 30° C. with stirring. On analysing the reaction solution by gc after 24 h, all the 1-bromo-3,4-methylenedioxybenzene had been consumed and the required arylboronic acid ester had formed. The amount of coupling (Suzuki reaction) that occurred was small (ratio of arylboronic acid ester:biaryl was ca. 100:4). Some debromination, giving 3,4-methylenedioxybenzene (1,3-benzodioxole), was also observed.

The reaction can be carried out in DMSO but the amount of dimer formed increases. Catalysts such as palladium acetate, bis(acetylacetonato)palladium (II) or palladium (10%) on carbon can also be used.

Example 42

Formation of

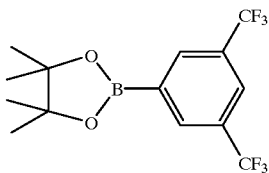

356 mgs (1.4 mmol) of bis(pinacolato)diboron, 25 mg of $PdCl_2(dppf).CH_2Cl_2$, 418 mg (3 mmol) $K_2CO_3$ and 290 mg (0.99 mmol) 3,5-bis(trifluoromethyl)bromobenzene were placed in a reaction tube under nitrogen. After addition of 5 ml dry ethanol, the reaction mixture was warmed to 30° C. with stirring. On analysing the reaction solution after 17 h, the reaction was essentially complete. The amount of coupling (Suzuki reaction) that occurred was small (ratio of arylboronic acid ester:biaryl was ca. 80:7).

The reaction between 3,5-bis(trifluoromethyl) bromobenzene and bis(pinacolato)diboron catalysed by $PdCl_2(dppf).CH_2Cl_2$ in the presence of K2CO3 also proceeds below 10° C.

When the reaction was carried out with dichloro(1,2-bis (diphenylphosphino)ethane)palladium (II), (21 mg), 283 mg (1. 11 mmol) bis(pinacolato)diboron 416 mg (3 mmol) $K_2CO_3$ and 287 mg (0.98 mmol) 3,5-bis(trifluoromethyl) bromobenzene in 5 ml ethanol at 30° C. for 19 h, the yield of the required arylboronic acid ester (by gc/fid detection, uncorrected for response factors) was 80% while the biaryl had formed to the extent of 4.5%.

Example 43

Formation of

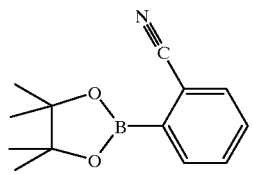

353 mgs (1.4 mmol) of bis(pinacolato)diboron, 25 mg of $PdCl_2(dppf).CH_2Cl_2$, 416 mg (3 mmol) $K_2CO_3$ and 231 mg (1.01 mmol) 2-iodobenzonitrile were placed in a reaction tube under nitrogen. After addition of 5 ml dry ethanol, the reaction was warmed to 30° C. with stirring. On analysing the reaction solution by gc after 17 h, the reaction was essentially complete. The yield of the required arylboronic acid ester (by gc/fid detection, uncorrected for response factors) was 44% while the biaryl had formed to the extent of 7% (ratio of ester:biaryl of 6:1). Reducing the reaction temperature to around 5–7° C., reduces the reaction rate but also the amount of biaryl formed (ratio of ester:biaryl of 14:1).

Example 44

Formation of

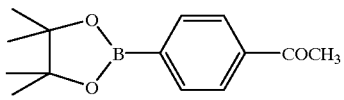

282 mgs (1.11 mmol) of bis(pinacolato)diboron, 25 mg of PdCl$_2$(dppf).CH$_2$Cl$_2$, 416 mg (3 mmol) K$_2$CO$_3$ and 246 mg (1.00 mmol) 4'-iodoacetophenone were placed in a reaction tube under nitrogen. After addition of 5 ml dry ethanol, the reaction was warmed to 30° C. with stirring. On analysing the reaction solution after 19 h, the reaction was essentially complete. The yield of the required arylboronic acid ester (by gc/fid detection, uncorrected for response factors) was 70% while the biaryl had formed to the extent of 3%.

Example 45

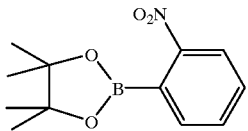

The formation of the boronic acid ester can be carried out at temperatures below ambient. Significant amount of the required arylboronic acid ester, with no detected dimer species, was obtained on reacting 1-bromo-2-nitrobenzene (202 mg, 1.0 mmol) with 280 mgs (1.10 mmol) of bis (pinacolato)diboron, 24 mg of PdCl$_2$(dppf).CH$_2$Cl$_2$, 411 mg (3 mmol) K$_2$CO$_3$ at 5–7° C. for 22 hr.

Example 46

One pot reaction

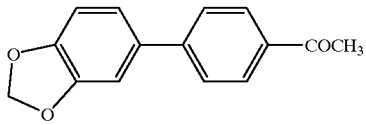

355 mgs (1.4 mmol) of bis(pinacolato)diboron, 25 mg of PdCl$_2$(dppf).CH$_2$Cl$_2$, 553 mg (4.0 mmol) K$_2$CO$_3$ and 249 mg (1.01 mmol) 4'-iodoacetophenone were placed in a reaction tube under nitrogen. After cooling the reaction tube in ice, 5 ml of methanol were added and the reaction kept between 5 and 7° C. with stirring. On analysing the reaction solution after 17.5 h, the reaction was complete with no detectable (by gc) amount of biaryl. After addition of 0.5 ml H$_2$O, the reaction was warmed to 60° C. with stirring for 4 h. Gc analysis of the reaction solution (0.3 ml aliquot) indicated that the excess bis(pinacolato)diboron had been destroyed by the aqueous base.

After addition of 260 mg (1.05 mol) 1-iodo-3,4-methylenedioxybenzene (excess), the reaction was continued at 60° C. for 16 h. All the arylboronic acid ester had reacted and the biaryl 3,4-methylenedioxy-4'-acetylbiphenyl had formed.

Example 47

One pot reaction

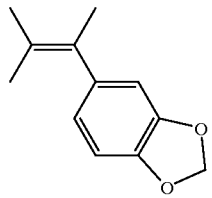

The arylboronic acid ester was formed at 30° C. by the reaction given in Example 41 above but using excess K$_2$CO$_3$ On addition of excess 2-bromo-3-methylbut-2-ene and increasing the reaction temperature to 60° C. for 6 h, the Suzuki coupling reaction was complete. The major peak in the gc was the desired coupled product.

Example 48

One pot reaction

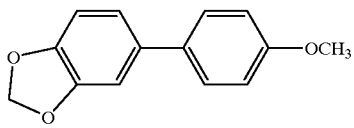

282 mgs (1.11 mmol) of bis(pinacolato)diboron, 25 mg of PdCl$_2$(dppf).CH$_2$Cl$_2$, 420 mg (3.0 mmol) K$_2$CO$_3$ and 234 mg (1.0 mmol) 4-iodoanisole were warmed with 5 ml methanol with stirring under an inert atmosphere in a reaction tube. On analysing the reaction solution by gc after 16 h, the 4-iodoanisole had all been consumed and the required arylboronic acid ester had formed. The ratio of bis(pinacolato)diboron, 2-(4-methoxyphenyl)-4,4,5,5-tetrarnethyl-1,3,2-dioxaborolane and 4,4'-dimethoxybiphenyl in the reaction solution was given by gc (fid detection) as, respectively, 2.9: 88.5: 1.4. The addition of 0.4 ml water and warming to 50° C. for several hr destroys the excess bis(pinacolato)diboron. After the addition of 257 mg (1.04 mmol) of 1-iodo-3,4-methylenedioxybenzene (excess), the reaction was continued at 50° C. for 16 h. All the arylboronic acid ester had reacted and the biaryl 3,4-methylenedioxy4'-methoxybiphenyl had formed.

This reaction can also be conveniently carried out without removal of excess bis(pinacolato)diboron when this reagent is used in near stoichiometric molar ratio for the synthesis of the arylboronic acid ester. Thus, reacting 267 mgs (1.05 mmol) of bis(pinacolato)diboron, 25 mg of PdCl$_2$(dppf). CH$_2$Cl$_2$, 416 mg (3.0 mmol) K$_2$CO$_3$ and 234 mg (1.0 mmol) 4-iodoanisole in 5 ml methanol at 25° C. for 16 h gave (by gc analysis) a 94% yield of the required ester (with 1.4% dimer) which was converted to the biphenyl by addition of 1-iodo-3,4-methylenedioxybenzene (excess, 315 mg, 1.27 mmol) and warming the mixture to 60° C. for 12 h. The ratio of 4,4'-dimethoxybiphenyl:4,4'-30 bis(1,3-benzodioxole) to asymmetric biaryl was 1:1.2:19. Some 4-methoxybiphenyl is also formed in the coupling reaction, presumably from the coupling of phenyl groups stemming from the catalyst phosphine ligand and the 4-methoxyphenyl from the boronic acid ester.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

What is claimed is:

1. A process for covalently coupling an aromatic ring compound with an organic compound which comprises the following steps:
   (i) reacting an aromatic ring compound having at a ring coupling position a halogen substituent or other substituent which undergoes substitution with a diboronic acid ester, with a diboronic acid ester in the presence of a Group VIII metal catalyst and a base which catalyzes, promotes or assists the reaction to form an arylboronic acid ester, said reaction proceeding by a substitution reaction between said diboronic acid ester and said halogen or other substituent of the aromatic ring compound, and
   (ii) reacting the arylboronic acid ester so formed with an organic compound having at a coupling position a halogen substituent or other substituent which undergoes substitution with the arylboronic acid ester, in the presence of a Group VIII metal catalyst and a base which catalyzes, promotes or assists the reaction, whereby the aromatic ring compound is coupled to the organic compound via a direct bond between respective coupling positions,
      wherein said aromatic ring compound has at least one further substituent selected from the group consisting of hydroxy, amino, imino, acetylene, carboxy, carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono, phosphonato, hydrohydroxyphosphoryl, allophanyl, guanidino, hydantoyl, ureido, and ureylene.

2. A process according to claim 1 which further comprises:
   adding water and a base after formation of the arylboronic acid ester to decompose unreacted diboronic acid ester, wherein said water and base is capable of decomposing the unreacted diboronic acid ester without adversely effecting subsequent reaction step(s).

3. A process for covalently coupling an aromatic ring compound with an organic compound which comprises the following steps:
   (i) reacting an aromatic ring compound having at a ring coupling position a halogen substituent or other substituent which undergoes substitution with a diboronic acid ester, with a diboronic acid ester in the presence of a Group VIII metal catalyst and a base which catalyzes, promotes or assists the reaction to form an arylboronic acid ester, said reaction proceeding by a substitution reaction between said diboronic acid ester and said halogen or other substituent of the aromatic ring compound, and
   (ii) reacting the arylboronic acid ester so formed with an organic compound having at a coupling position a halogen substituent or other substituent which undergoes substitution with the arylboronic acid ester, in the presence of a Group VIII metal catalyst and a base which catalyzes, promotes or assists the reaction, whereby the aromatic ring compound is coupled to the organic compound via a direct bond between respective coupling positions,
      wherein said reactions are conducted in the presence of a protic solvent selected from water and lower alcohols.

4. A process for covalently coupling an aromatic ring compound with an organic compound which comprises the following steps:
   (i) reacting an aromatic ring compound having at a ring coupling position a halogen substituent or other substituent which undergoes substitution with a diboronic acid ester, with a diboronic acid ester in the presence of a Group VIII metal catalyst and a base which catalyzes, promotes or assists the reaction to form an arylboronic acid derivative, said reaction proceeding by a substitution reaction between said diboronic acid ester and said halogen or other substituent of the aromatic ring compound, said reaction being conducted at a temperature which is sufficiently low to prevent coupling of the arylboronic acid ester with the aromatic ring compound,
   (ii) reacting the arylboronic acid ester with an added organic compound having at a coupling position a halogen substituent or other substituent which undergoes substitution with the arylboronic acid derivative, in the presence of a Group VIII metal catalyst and a base which catalyzes, promotes or assists the reaction, whereby the aromatic ring compound is coupled to the organic compound via a direct bond between respective coupling positions,
      said coupling reaction of the arylboronic acid ester with the organic compound being promoted by raising the temperature relative to the temperature at which step (i) is conducted.

5. A process for covalently coupling an aromatic ring compound with an organic compound which comprises the following steps:
   (i) reacting an aromatic ring compound having at a ring coupling position a halogen substituent or other substituent which undergoes substitution with a diboronic acid ester, with a diboronic acid ester in the presence of a Group VIII metal catalyst and a base which catalyzes, promotes or assists the reaction to form an arylboronic acid ester, said reaction proceeding by a substitution reaction between said diboronic acid ester and said halogen or other substituent of the aromatic ring compound, and
   (ii) reacting the arylboronic acid ester so formed with an organic compound having at a coupling position a halogen substituent or other substituent which undergoes substitution with the arylboronic acid ester, in the presence of a Group VIII metal catalyst and a base which catalyzes, promotes or assists the reaction, whereby the aromatic ring compound is coupled to the organic compound via a direct bond between respective coupling positions,
      wherein water and a base are added after step (i) to decompose unreacted diboronic acid ester, wherein said base is capable of decomposing the unreacted diboronic acid ester without adversely effecting the subsequent reaction step(s).

6. A process according to claim 5 wherein said base used to decompose excess diboronic acid ester is also used to catalyze step (ii).

7. A process according to claim 5 wherein the base for step (i) is selected from the group consisting of aryl and alkyl carboxylates, fluorides, hydroxides and carbonates of Li, Na, K, Rb, Cs, ammonium, alkylammonium, Mg, Ca and Ba; phosphates, and arylphosphates of Li, Na, K, Rb and Cs; phosphate esters of Li, Na, K, Rb and Cs, phenoxides of Li, Na, K, Rb and Cs; alkoxides of Li, Na, K, Rb and Cs; and thallium hydroxide.

8. A process according to claim 5 wherein the organic compound is different from the aromatic ring compound.

9. A process according to claim 5 wherein the aromatic ring compound is the same as the organic compound.

10. A process according to claim 5 conducted in a single pot.

11. A process according to claim 5 wherein the arylboronic acid ester is isolated prior to reaction with the organic compound.

12. A process according to claim 5 wherein the organic compound is an olefinic compound having at a vinylic coupling position a halogen substituent, or other substituent capable of undergoing substitution with the diboronic acid ester.

13. A process according to claim 5 wherein either one or both of the aromatic ring compound and the organic compound has more than one halogen or other substituent capable of undergoing substitution with a diboronic acid ester.

14. A process according to claim 5 wherein the Group VIII metal catalyst comprises palladium, nickel or platinum.

15. A process according to claim 14 wherein the Group VIII metal catalyst is a palladium catalyst.

16. A process according to claim 15 wherein the palladium catalyst is a palladium complex.

17. A process according to claim 14 wherein the catalyst is a nickel complex.

18. A process according to claim 16 wherein the palladium complex is selected from the group consisting of $PdCl_2$, $Pd(OAc)_2$, $PdCl_2(1,1'-bis(diphenylphosphinoferrocene),CH_2Cl_2$, $Pd(PPh_3)_4$, $Pd(Ph_2P(CH_2)_nPPh_2)$ where n is 2, 3 or 4, and related catalysts which are complexes of palladium with phosphine ligands.

19. A process according to claim 15 wherein the catalyst is selected from the group consisting of palladium black, palladium on carbon, palladium clusters and palladium in porous glass.

20. A process according to claim 14 wherein the catalyst is selected from the group consisting of nickel black, Raney nickel, nickel on carbon and nickel clusters.

21. A process according to claim 5 wherein the diboronic acid ester is a compound of the formula:

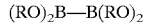

wherein R is optionally substituted alkyl or aryl or —B(OR)$_2$ represents a cyclic group of the formula

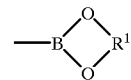

where R$^1$ is optionally substituted alkylene, arylene or other divalent group comprising linked aromatic and aliphatic moieties.

22. A process according to claim 21 wherein the diboronic acid ester is selected from the group consisting of the pinacol ester of diboronic acid, bis(ethanediolato) diboron, bis(n-propanediolato) diboron and bis(neopentyldiolato) diboron.

23. A process according to claim 4 conducted in the presence of a protic solvent.

24. A process according to claim 3 conducted in the presence of a protic solvent which is water, a lower alcohol or a mixture thereof.

25. A process according to claim 24 wherein the protic solvent is water, methanol, ethanol, isopropanol or a mixture thereof.

26. A process according to claim 5 wherein the aromatic ring compound has a further substituent selected from the group consisting of hydroxy, amino, imino, acetyleno, carboxy, carboxylato, carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono, phosphonato, hydrohydroxyphosphoryl, allophanyl, guanidino, hydantoyl, ureido, and ureylene.

27. A process according to claim 5 conducted at a temperature between 0° and 120° C.

28. A process of claim 27 wherein the temperature is in the range of 15 ° to 40° C.

29. A process according to claim 5 wherein the base of step (i) is capable of catalyzing reaction of the aromatic ring compound with the diboronic acid ester, but not strong enough to catalyze the further reaction of the arylboronic acid ester with the organic compound.

30. A process of claim 29 wherein the base of step (i) is selected from the group consisting of aryl and alkyl carboxylates and phosphates of Li, Na, K, Rb, Cs, ammonium and alkylammonium.

31. A process of claim 1 wherein the base of steps (i) and/or step (ii) is selected from the group consisting of aryl and alkyl carboxylates, fluorides, hydroxides and carbonates of Li, Na, K, Rb, Cs, ammonium, alkylammonium, Mg, Ca and Ba; phosphates, and arylphosphates of Li, Na, K, Rb and Cs; phosphate esters of Li, Na, K, Rb and Cs, phenoxides of Li, Na, K, Rb and Cs; alkoxides of Li, Na, K, Rb and Cs; and thallium hydroxide.

32. A process of claim 31 wherein the base utilized in step (ii) is selected from cesium carbonate, potassium carbonate and alkali metal hydroxides.

33. A process according to claim 5 wherein one of said aromatic ring compound and said organic compound is a polymer.

34. A process according to claim 5 wherein one of said aromatic ring compound and said organic compound is chemically linked to a solid polymer support.

35. A process according to claim 5 wherein the organic compound reacted with the aryl boronic acid ester in step (ii) is an aromatic ring compound having a halogen substituent, or other substituent capable of undergoing a substitution with the diboronic acid ester.

36. A process according to claim 4 wherein the sufficiently low temperature is ambient temperature or below.

37. A process according to claim 4 wherein the sufficiently low temperature is below 0° C.

38. A process according to claim 4 wherein the base of step (i) is the same as the base of step (ii).

39. A process according to claim 4 wherein the sufficiently low temperature is below 40° C.

40. A process according to claim 18 wherein the palladium complex is a complex of palladium with a phosphine ligand selected from the group consisting of P(o-tolyl)$_3$, P(i-Pr)$_3$, P(cyclohexyl)$_3$, P(o-MeOPh)$_3$, P(p-MeOPh)$_3$, bis(diphenylphosphino)propane, bis(diphenylphosphino)butane, tri(2,6-dimethoxyphenyl)phosphine, tri(2,4,6,trimethoxyphenyl)phosphine, trimethylolpropane phosphite, 4-ethyl-2,6,7-trioxa-1-phospho-bicyclo[2.2.2]octane, tri(m-sulfophenyl)phosphine and related water soluble phosphines.

41. A process according to claim 18 wherein the palladium complex is a complex of palladium with a ligand selected from the group consisting of tri-o-tolyl-phosphine, tri-1-propylphosphine, tricyclohexylphosphine, tris(o-methoxy-phenyl)phosphine, tris(p-methoxyphenyl)phosphine, 1,3-bis(diphenyl-phosphino)propane, 1,4-bis(diphenylphosphino)butane, tri(2,6-dimethoxyphenyl)phosphine, tri(2,4,6-trimethoxyphenyl)phosphine, 4-ethyl-2,6,7-trioxa-1-phospho-bicyclo [2.2.2]octane and tri(m-sulfophenyl)phosphine.

42. A process according to claim 1 wherein the other substituent which undergoes substitution with a diboronic acid ester is a triflate, mesylate, diazonium salt or phosphate.

43. A process according to claim 3 wherein the other substituent which undergoes substitution with a diboronic acid ester is a triflate, mesylate, diazonium salt or phosphate.

44. A process according to claim 4 wherein the other substituent which undergoes substitution with a diboronic acid ester is a triflate, mesylate, diazonium salt or phosphate.

45. A process according to claim 5 wherein the other substituent which undergoes substitution with a diboronic acid ester is a triflate, mesylate, diazonium salt or phosphate.

* * * * *